United States Patent
Akthakul et al.

(10) Patent No.: US 12,257,338 B2
(45) Date of Patent: Mar. 25, 2025

(54) COMPOSITIONS AND METHODS FOR APPLICATION OVER SKIN

(71) Applicant: SHISEIDO COMPANY, LIMITED, Tokyo (JP)

(72) Inventors: Ariya Akthakul, Boston, MA (US); Nithin Ramadurai, Wakefield, MA (US)

(73) Assignee: Shiseido Company, Limited, Tokyo (JP)

( * ) Notice: Subject to any disclaimer, the term of this patent is extended or adjusted under 35 U.S.C. 154(b) by 236 days.

(21) Appl. No.: 17/273,492

(22) PCT Filed: Sep. 26, 2019

(86) PCT No.: PCT/JP2019/039031
§ 371 (c)(1),
(2) Date: Mar. 4, 2021

(87) PCT Pub. No.: WO2020/067582
PCT Pub. Date: Apr. 2, 2020

(65) Prior Publication Data
US 2021/0338562 A1    Nov. 4, 2021

Related U.S. Application Data

(60) Provisional application No. 62/737,652, filed on Sep. 27, 2018.

(51) Int. Cl.
| | | |
|---|---|---|
| *A61K 8/895* | (2006.01) | |
| *A61K 8/02* | (2006.01) | |
| *A61K 8/25* | (2006.01) | |
| *A61K 9/00* | (2006.01) | |
| *A61K 31/80* | (2006.01) | |
| *A61K 45/06* | (2006.01) | |
| *A61Q 19/00* | (2006.01) | |

(52) U.S. Cl.
CPC ............ *A61K 8/895* (2013.01); *A61K 8/0204* (2013.01); *A61K 8/25* (2013.01); *A61K 9/0014* (2013.01); *A61K 31/80* (2013.01); *A61K 45/06* (2013.01); *A61Q 19/00* (2013.01); *A61K 2800/882* (2013.01); *A61K 2800/95* (2013.01)

(58) Field of Classification Search
None
See application file for complete search history.

(56) References Cited

U.S. PATENT DOCUMENTS

| | | |
|---|---|---|
| 3,261,802 A | 7/1966 | Bobear et al. |
| 3,419,006 A | 12/1968 | King |
| 3,635,743 A | 1/1972 | Smith |
| 3,882,083 A | 5/1975 | Berger et al. |
| 3,884,866 A | 5/1975 | Jeram et al. |
| 3,950,300 A | 4/1976 | Hittmair et al. |
| 3,957,713 A | 5/1976 | Jeram et al. |
| 4,013,611 A | 3/1977 | Hechtl et al. |
| 4,025,485 A | 5/1977 | Kodama et al. |
| 4,683,278 A | 7/1987 | Toshio |
| 4,908,140 A | 3/1990 | Bausch et al. |
| 5,173,291 A | 12/1992 | Brink |
| 5,190,827 A | 3/1993 | Lin |
| 5,219,560 A | 6/1993 | Suzuki et al. |
| 5,525,344 A | 6/1996 | Wivell |
| 5,534,609 A | 7/1996 | Lewis et al. |
| 5,616,632 A | 4/1997 | Fujiki et al. |
| 5,800,816 A | 9/1998 | Brieva et al. |
| 5,830,951 A | 11/1998 | Fiedler |
| 5,919,437 A | 7/1999 | Lee et al. |
| 5,919,468 A | 7/1999 | Bara et al. |
| 5,922,470 A | 7/1999 | Bracken et al. |
| 5,955,513 A | 9/1999 | Hare |
| 6,066,326 A | 5/2000 | Afriat et al. |
| 6,313,190 B1 | 11/2001 | Bublewitz et al. |
| 6,342,237 B1 | 1/2002 | Bara et al. |

(Continued)

FOREIGN PATENT DOCUMENTS

| | | |
|---|---|---|
| CN | 103920179 | 7/2014 |
| CN | 106236608 | 12/2016 |

(Continued)

OTHER PUBLICATIONS

International Preliminary Report on Patentability dated Mar. 23, 2021 for PCT/JP2019/039031 (9 pages).
English Translation of Office Action mailed Nov. 26, 2023 in corresponding Taiwan Application No. 108134831.
Agache et al., "Mechanical properties and Young's modulus of human skin in vivo," Archives of Dermatological Research, 269:3 (1980) 221-232.
Andisil XL Two Part RTV, one page, Revision Date Feb. 2022. Downloaded Mar. 13, 2023.

(Continued)

*Primary Examiner* — Patricia Duffy
*Assistant Examiner* — Garen Gotfredson
(74) *Attorney, Agent, or Firm* — Jones Day

(57) ABSTRACT

Disclosed herein are compositions that can form a covering, layer, film, device, and/or prosthetic skin that can be comfortably worn to provide skin barrier function, skin hydration and therapeutic and aesthetic benefits. Provided herein are novel compositions that have low tackiness and form quickly, resulting in a wearable, comfortable (maintains temperature and humidity), breathable, thin, optically invisible, cosmetically elegant, flexible, stretchable, elastic and body-movement conforming, yet long-lasting covering, layer, film, device, and/or prosthetic skin on the skin or any other body surface. Provided herein are novel compositions that can form a covering, layer, film, device, and/or prosthetic skin that works for extended periods in excess of about 24 hours, while retaining function during and after exercising, showering and swimming (in sea-water, fresh water and chlorinated water), steam room (heat at high humidity), and sauna (heat at low humidity).

20 Claims, No Drawings

(56) References Cited

U.S. PATENT DOCUMENTS

| | | |
|---|---|---|
| 6,355,724 B1 | 3/2002 | LeGrow et al. |
| 6,391,944 B2 | 5/2002 | Canoont et al. |
| 6,423,322 B1 | 7/2002 | Fry et al. |
| 6,471,985 B2 | 10/2002 | Guyuron et al. |
| 6,512,072 B1 | 1/2003 | Gantner et al. |
| 6,544,532 B1 | 4/2003 | Jager-Lezer et al. |
| 6,545,076 B2 | 4/2003 | Kaiya et al. |
| 6,573,299 B1 | 6/2003 | Petrus |
| 6,613,185 B1 | 9/2003 | Valade et al. |
| 6,682,749 B1 | 1/2004 | Potechin et al. |
| 6,762,242 B1 | 7/2004 | Torto et al. |
| 6,998,427 B2 | 2/2006 | Del Torto et al. |
| 7,078,026 B2 | 7/2006 | Ferrari et al. |
| 7,083,800 B1 | 8/2006 | Terren et al. |
| 7,148,306 B2 | 12/2006 | Frank et al. |
| 7,270,828 B2 | 9/2007 | Masuda et al. |
| 7,273,658 B2 | 9/2007 | Benayoun et al. |
| 7,335,708 B2 | 2/2008 | Bublewitz et al. |
| 7,425,292 B2 | 9/2008 | Yang et al. |
| 7,452,957 B2 | 11/2008 | Curtis |
| 7,482,419 B2 | 1/2009 | Caprasse et al. |
| 7,572,514 B2 | 8/2009 | Howe et al. |
| 7,750,106 B2 | 7/2010 | Zheng et al. |
| 8,034,323 B2 | 10/2011 | Zheng et al. |
| 8,133,478 B2 | 3/2012 | Maitra et al. |
| 8,263,055 B2 | 9/2012 | Do |
| 8,569,792 B2 | 10/2013 | Mitani et al. |
| 8,611,746 B2 | 12/2013 | Pincemin et al. |
| 8,658,755 B2 | 2/2014 | Saito |
| 8,691,202 B2 | 4/2014 | Yu et al. |
| 8,920,783 B2 | 12/2014 | Lin |
| 8,952,118 B2 | 2/2015 | Arkles et al. |
| 9,044,288 B2 | 6/2015 | Angeletakis |
| 9,096,721 B2 | 8/2015 | Garaud et al. |
| 9,114,096 B2 | 8/2015 | Yu et al. |
| 9,186,315 B2 | 11/2015 | Singer |
| 9,308,221 B2 | 4/2016 | Yu et al. |
| 9,333,223 B2 | 5/2016 | Yu et al. |
| 9,511,034 B1 | 12/2016 | Garrett |
| 9,724,363 B2 | 8/2017 | Yu et al. |
| 9,937,200 B2 | 4/2018 | Yu et al. |
| 10,022,396 B2 | 7/2018 | Yu et al. |
| 10,918,661 B2 | 2/2021 | Yu et al. |
| 10,973,848 B2 | 4/2021 | Yu et al. |
| 11,160,827 B2 | 11/2021 | Akthakul et al. |
| 2002/0022040 A1 | 2/2002 | Robinson et al. |
| 2002/0122771 A1 | 9/2002 | Holland et al. |
| 2003/0180281 A1 | 9/2003 | Bott et al. |
| 2004/0258628 A1 | 12/2004 | Riedel et al. |
| 2005/0148727 A1 | 7/2005 | Ajbani et al. |
| 2005/0158260 A1 | 7/2005 | Ferrari et al. |
| 2005/0175562 A1 | 8/2005 | Hadasch et al. |
| 2005/0261632 A1 | 11/2005 | Xu |
| 2006/0029623 A1 | 2/2006 | Astruc et al. |
| 2007/0142575 A1 | 6/2007 | Zheng et al. |
| 2007/0142599 A1 | 6/2007 | Zheng et al. |
| 2007/0212314 A1 | 9/2007 | Murphy et al. |
| 2007/0244230 A1 | 10/2007 | Sixt et al. |
| 2007/0292463 A1 | 12/2007 | Spector |
| 2008/0102050 A1 | 5/2008 | Li et al. |
| 2008/0159970 A1 | 7/2008 | Willemin |
| 2008/0279797 A1 | 11/2008 | Maitra et al. |
| 2008/0281055 A1 | 11/2008 | Schlitzer et al. |
| 2009/0035246 A1 | 2/2009 | Do |
| 2009/0214455 A1 | 8/2009 | Blin et al. |
| 2009/0317343 A1 | 12/2009 | Lin et al. |
| 2010/0112019 A1 | 5/2010 | Thevenet |
| 2010/0152135 A1 | 6/2010 | Blin et al. |
| 2010/0178266 A1 | 7/2010 | Huggins et al. |
| 2010/0179105 A1 | 7/2010 | Blin et al. |
| 2011/0040242 A1 | 2/2011 | Fallon et al. |
| 2011/0166275 A1 | 7/2011 | Zhang |
| 2011/0170864 A1 | 7/2011 | Tani et al. |
| 2012/0237461 A1 | 9/2012 | Yu et al. |
| 2012/0251600 A1 | 10/2012 | Yu et al. |
| 2013/0052356 A1 | 2/2013 | Li et al. |
| 2013/0078209 A1 | 3/2013 | Yu et al. |
| 2013/0178571 A1 | 7/2013 | Ogawa et al. |
| 2014/0004065 A1 | 1/2014 | Souda et al. |
| 2014/0004073 A1 | 1/2014 | Yu et al. |
| 2014/0010769 A1 | 1/2014 | Lomakin et al. |
| 2014/0044670 A1 | 2/2014 | Yu et al. |
| 2014/0275406 A1 | 9/2014 | Arkles et al. |
| 2014/0322519 A1 | 10/2014 | Ahn et al. |
| 2015/0190516 A1 | 7/2015 | Cauvin et al. |
| 2015/0274971 A1 | 10/2015 | Endo et al. |
| 2015/0284590 A1 | 10/2015 | Endo et al. |
| 2016/0143840 A1 | 5/2016 | Yu et al. |
| 2016/0250250 A1 | 9/2016 | Yu et al. |
| 2016/0317574 A1 | 11/2016 | Yu et al. |
| 2017/0189317 A1 | 7/2017 | Bernard et al. |
| 2017/0360824 A1 | 12/2017 | Yu et al. |
| 2017/0368094 A9 | 12/2017 | Yu et al. |
| 2018/0256636 A1 | 9/2018 | Yu et al. |
| 2018/0296591 A1 | 10/2018 | Yu et al. |
| 2020/0009184 A1 | 1/2020 | Akthakul et al. |
| 2021/0213046 A1 | 7/2021 | Akthakul et al. |
| 2021/0213047 A1 | 7/2021 | Akthakul et al. |
| 2021/0252041 A1 | 8/2021 | Akthakul et al. |
| 2021/0338562 A1 | 11/2021 | Akthakul et al. |
| 2022/0062327 A1 | 3/2022 | Yu et al. |
| 2022/0176013 A1 | 6/2022 | Akthakul et al. |

FOREIGN PATENT DOCUMENTS

| | | |
|---|---|---|
| CN | 106236608 A | 12/2016 |
| EP | 0445982 | 9/1991 |
| EP | 0851000 | 7/1998 |
| EP | 0865787 | 9/1998 |
| EP | 2090294 | 8/2009 |
| FR | 2894817 | 6/2007 |
| FR | 2910291 | 6/2008 |
| FR | 2954143 | 6/2011 |
| FR | 2956319 | 8/2011 |
| JP | 2009/520002 | 5/2009 |
| WO | WO 2000/074738 | 12/2000 |
| WO | WO 2007/071886 | 6/2007 |
| WO | WO 2007/102859 | 9/2007 |
| WO | WO 2007/117284 | 10/2007 |
| WO | WO 2008/075282 | 6/2008 |
| WO | WO 2009/042732 | 4/2009 |
| WO | WO 2009/090074 | 7/2009 |
| WO | WO 2009/090242 | 7/2009 |
| WO | WO 2011/001217 | 1/2011 |
| WO | WO 2012/030984 | 3/2012 |
| WO | WO 2012/030993 | 3/2012 |
| WO | WO 2013/044098 | 3/2012 |
| WO | WO 2013/070302 | 5/2013 |
| WO | WO 2013/076450 | 5/2013 |
| WO | WO 2013/158844 | 10/2013 |
| WO | WO 2015/068859 | 5/2015 |
| WO | WO 2017/083398 | 5/2017 |
| WO | WO 2017/117438 | 7/2017 |
| WO | WO 2020/067582 | 4/2020 |
| WO | WO 2020/212828 | 10/2020 |

OTHER PUBLICATIONS

Andisil: Specialty Silicones for Dental Solutions (www.andisil.com/test-site.com/wp-content/uploads/2017/12/ABSS-Silicone-for-Dental-Applications.pdf); 8 pages; upload dated Dec. 2017.

Brook et al. (2007) "Pretreatment of Liquid Silicone Rubbers to Remove Volatile Siloxanes," Ind. Enq. Chem. Res. 46:8796-8805.

Correct Combo, [retrieved on Dec. 10, 2014 from on-line website http://www.d ruas.com/otc/122754/correct-com bo.html].

Croll, S.G., "Adhesion Loss Due to Internal Strain," Journal of Coatings Technology, 52:665 (1980) 35-43.

Francis et al., "Development and measurement of stress in polymer coatings," Journal of Materials Science, 37 (2002) 4717-4731.

Fumed Silica: retrieved from internet: http://www.powerchemcorp.com/library/public/fumed_silica/SiSiB_Fumed_Silica.pdf. Retrieved on Sep. 4, 2016.

(56) References Cited

OTHER PUBLICATIONS

Gelest, Safety Data Sheet HMS-301 (2014) pp. 1-5.
Grahame, "A Method for Measuring Human Skin Elasticity in Vivo with Observations on the Effects of Age, Sex and Pregnancy," Clinical Science, 39 (1970) 223-238.
Herrling et al., "Cerium Dioxide: Future UV-filter in Sunscreen," retrieved from the internet on Aug. 6, 2018: < http://www.gematria-test-lab.com/pdf_2013/article05-2013.pdf>.
Hwang, S.M et al. (2001). "Basis of Occlusive Therapy in Psoriasis: Correcting Defects in Permeability Barrier and Calcium Gradient," International Journal of Dermatology 40:223-231.
Jachowicz et al., "Alteration of skin mechanics by thin polymer films," Skin Research and Technology, 14:3 (2008) 312-319.
Johnson Matthey Online Catalog, "Karstedt Catalysts", CAS No. 68478-92-2, retrieved from the internet on Apr. 21, 2021 at <https://matthey.com/en/products-and-services/previous-metal-chemicals/platinum-chemicals/karstedt-catalysts> 3 pages.
Klykken, P. et al. (2004). "Silicone Film-Forming Technologies for Health Care Applications," Dow Corning; 8pp.
Leow, Y-H et al. (1997, e-pub. Jul. 12, 2009). "Effect of Occlusion on Skin," Journal of Dermatoloaical Treatment 8(2):139-142.
Liquid Silicone Rubber: Global Product Selection Guide: retrieved from internet: https://www.dowcorning.com/content/publishedlit/95-1226-lsr-selection-guide.pdf. Retrieved on Sep. 4, 2016.
Ostergaard, Dow Corning SA, Next Generation Rheology Control rings New Formulation Options for Personal Care, pp. 1-6:2008.
Quartz Powder: retrieved from internet: http://www.cosmeticanalysis.com/cosmeticinaredients/auartz-powder.html. Retrieved on Sep. 3, 2016.
Ritzhaupt-Kleissl et al., "Material Properties of Polymer Nanoparticle Composites for Micro Optical Applications," NSTI-Nanotech, vol. 2 (2006) 852-855.
Sigma-Aldrich, Poly (dimethylsiloxane-co-methylhydrosiloxane), trimethylsilyl terminated Product Sheet, poly(dimethylsiloxane-co-methylhydrosiloxane) trimethylsilyl terminated, http://www.sigmaaldrich.com/eatafog/product/aldrieh/482196?lang-en&reigion=US, last accessed Sep. 11, 2017.
Silc Pig: retrieved from internet: https://www.smooth-on.com/product-line/silc-pig/. Retrieved on Sep. 4, 2016.
Silicones Plus product list [retrieved Dec. 10, 2014 on-line] Website: http://siliconesplus.com/storaae/Silicones%_20Pius%20Brochure_1.pdf.
TraumaSkin FX™ Platinum Silicone Sculpting/Casting Medium: retrieved from internet: http://web.archive.org/web/20100407000529/http://www.paintandpowderstore.com/products.php?cat=47. Retrieved on Sep. 4, 2016.

TraumaSkin FX™ Platinum Silicone Sculpting/Casting Medium: retrieved from internet: http://web.archive.org/web/201004008110519/http://www.paintandpowderstore.com/proddetail.php?prod =MM-1002&cat=47. Retrieved on Apr. 25, 2017.
Yu, Betty et al., "An Elastic Second Skin," Nature Materials (May 9, 2016) pp. 1-10.
Zhai, H. et al. (2001). "Effects of Skin Occlusion on Percutaneous Absorption: An Overview," Skin Pharmacol Appl Skin Physiol 14(1):1-10.
Zhai, H. et al. (2002) "Occlusion vs. Skin Barrier Function," Skin Research and Technology 8:1-6.
Zou, Xuefeng et al., "Mechanisms of the Antimicrobial Activities of Graphene Materials," *Journal of the American Chemical Society*, 138 (2016) 2064-2077.
Zuo, Yujing et al., "Sunlight-induced cross-linked luminescent films based on polysiloxanes and D-Limonene via Thiol-ene "Click" Chemistry", *Adv. Funct. Mater.*, 25:18 (2015) 2754-2762.
European Search Report mailed Mar. 16, 2015 in corresponding Application No. EP11822576.
Extended European Search Report dated Aug. 27, 2019 for European App. No. 16864921.8.
International Search Report mailed Apr. 19, 2012 for International Application No. PCT/US2011/050003.
International Search Report mailed Apr. 30, 2012 for International Application No. PCT/US2011/050016.
Written Opinion mailed Apr. 30, 2012 for International Application No. PCT/US2011/050016.
International Preliminary Report on Patentability mailed Mar. 5, 2013 for International Application No. PCT/US2011/050016.
International Search Report mailed Dec. 3, 2012 for International Application No. PCT/US2012/056667.
Written Opinion mailed Dec. 3, 2012 for International Application No. PCT/US2012/056667.
International Preliminary Report on Patentability mailed Mar. 25, 2014 for International Application No. PCT/US2012/056667.
International Search Report mailed Nov. 13, 2014 for International Application No. PCT/US2013/037116.
International Search Report mailed Jan. 25, 2017 for International Application No. PCT/US2016/061150.
Written Opinion mailed Jan. 25, 2017 for International Application No. PCT/US2016/061150.
International Preliminary Report on Patentability dated Mar. 23, 2021 for International Application No. PCT/JP2019/039031 (8 pages).
Japanese Office Action dated Apr. 5, 2022 for Application No. JP 2021-118522 (with English translation).
Japanese Office Action, Application No. JP 2013-527273, date of mailing Jun. 23, 2015 (with English translation).

COMPOSITIONS AND METHODS FOR APPLICATION OVER SKIN

This application is a U.S. National Stage Application of International Application No. PCT/JP2019/039031, which claims the benefit of U.S. Provisional Application No. 62/737,652, filed Sep. 27, 2018, which are incorporated herein by reference in their entireties.

1 FIELD

Provided herein are compositions, devices and methods for modifying skin function and appearance and protecting skin by the formation of a layer over the skin of a subject that forms quickly and that is thin, durable, non-invasive, easy to use, and with skin-like properties.

2 BACKGROUND

International Application Publication Nos. WO2012/030984, WO2012/030993, WO2013/044098 and WO2017/083398 disclosed compositions and polymer materials suitable for skincare products for cosmetic and therapeutic applications. The synthesis and application of an elastic, wearable crosslinked polymer layer (XPL) that mimics the properties of normal, youthful skin have been described in Yu, Betty, et al. "An elastic second skin," *Nature materials* 15.8 (2016): 911.

Current methods for reducing the appearance of skin imperfections, for example wrinkles, fine lines, age spots, enlarged pores or scars, include invasive and non-invasive methods and compositions. Invasive techniques, such as surgery, fillers (e.g., Restylane, Juvederm), laser resurfacing or Botox®, may provide longer-lasting effects and can treat prominent imperfections. However, many consumers either cannot afford or do not wish undergo such drastic cosmetic treatments.

Examples of non-invasive methods include hiding imperfections by applying a foundation-type make-up to the skin or applying a cosmetic composition that includes an ingredient that may reduce the appearance of the imperfections over time (e.g., an anti-wrinkle cream). Unfortunately, foundation make-up is not durable and cannot reduce the appearance of pronounced skin imperfections, such as deep wrinkles or scars, while cosmetic compositions containing ingredients that may reduce the appearance of an imperfection take time to produce an effect, and also may not reduce the appearance of a pronounced imperfection. In particular, many current cosmetic compositions do not have the required mechanical properties to reduce the appearance of pronounced imperfections.

High molecular weight polymers, including proteins and polysaccharides, have been used in attempts to develop anti-aging skin care cosmetic compositions (Jachowicz et al., *Skin Res. and Tech.*, 2008, 14:312-319). While these polymers change the physical properties (e.g., elasticity and stiffness) of the skin upon application to the skin, they did not provide the durability to enable natural, repeated facial motion for extended wear. The commercially available polymer materials used in skincare products today do not necessarily provide the elasticity, environmental resistance and skin adhesion for long lasting product performance nor do they provide the aesthetic feel and appearance required by the consumer of cosmetic products.

The skin acts as a protective barrier from the external environment. When damaged, a cascade of events is triggered to repair to the damaged tissue. Wound healing is a complex process, progressing through four stages (inflammation, proliferation, remodeling, and epithelialization) to repair the damaged area. Although wound healing is a natural process, disruption of the events involved may lead to incomplete healing and further damage to the tissue. Current methods of treating wounds include applying a dressing to the wound to stem bleeding, prevent infection and encourage healing. Wound dressings are often made from breathable material (for example, gauze). Occlusive dressings have been used on wounds, but the effects of occlusion on wounded skin are not completely understood (see e.g., Leow and Maibach; *J Dermatol Treat*, (1997) 8, 139-142). However, current methods of using occlusion on wounded skin is unsatisfactory because current occlusive dressings are not durable, convenient, or long lasting. Moreover, some current occlusive coverings require subjects to wrap plastic around the area to be treated, lowering subject compliance because the treatment is cumbersome and uncomfortable. Lastly, current occlusive coverings do not permit the exposure of the wound to the environment to be modulated based upon the nature of the wound. For example, current occlusive dressings are designed to exclude both air and water, and generally it is not possible to permit exposure to one and not the other. The commercially available polymer materials used in therapeutic products today do not necessarily provide the elasticity, environmental resistance and skin adhesion for long lasting product performance nor do they provide the aesthetic feel and appearance required by the consumer of therapeutic products.

Accordingly, there remains a need for compositions, devices and methods for modifying skin function and appearance and protecting skin.

3 SUMMARY

Provided herein are compositions for the formation of a film over the skin of a subject, comprising: a) a bifunctional organopolysiloxane polymer having one unsaturated group and one hydride group; and b) a reinforcing constituent suitable for formation of a film on the subject's skin. In one embodiment, the bifunctional organopolysiloxane polymer is a linear siloxane polymer. In one embodiment, the bifunctional organopolysiloxane polymer is a branched siloxane polymer. In one embodiment, the unsaturated group or the hydride group are terminal groups. In one embodiment, the linear siloxane polymer has a degree of polymerization of at least 20 and a dispersity index less than about 1.2, and wherein a ratio of unsaturated terminal groups to hydride terminal groups is substantially 1:1. In one embodiment, the degree of polymerization is about 20 to about 200. In one embodiment, the unsaturated terminal group is selected from the group consisting of vinyl, styryl, allyl, methallyl, hexenyl, octenyl and alkynyl. In one embodiment, the bifunctional organopolysiloxane polymer has a siloxane backbone selected from the group consisting of diphenylsiloxane, phenylmethylsiloxane, trifluoropropylmethylsiloxane, dimethylsilylethylsiloxane, and alkylmethylsiloxane. In one embodiment, the siloxane backbone is dimethylsiloxane and the unsaturated group is vinyl. In one embodiment, the film has no apparent crosslinking. In one embodiment, the linear siloxane polymer is a monovinyl-monohydride terminated polysiloxane. In one embodiment, the film is formed via hydrosilylation step-growth polymerization of the linear siloxane polymer. In one embodiment, the linear siloxane polymer is capable of being reacted with a metal catalyst to form the film over the subject's skin. In one embodiment, the metal catalyst is a platinum catalyst. In one embodiment, the reinforcing constituent is fumed silica. In one embodiment, the linear siloxane polymer is a monovinyl-monohydride terminated polydimethylsiloxane. In one embodiment, the reinforcing constituent is selected from the group consisting of optionally surface treated mica, zinc oxide, titanium dioxide, aluminum oxide, clay or silica.

In one embodiment, the composition further comprises an agent, wherein the agent is anti-oxidants, vitamins, vitamin D3 analogues, retinoids, minerals, mineral oil, petroleum jelly, fatty acids, plant extracts, polypeptides, antibodies, proteins, sugars, humectants, emollients, or a combination thereof.

In one embodiment, the composition further comprises an agent, wherein the agent is a cosmetic agent. In one embodiment, the cosmetic agent is a moisturizer, a sunscreen, a UV protecting agent, a skin-protectant agent, a skin-soothing agent, a skin-lightening agent, a skin-brightening agent, a skin-softening agent, a skin-smoothening agent, a skin-bleaching agent, a skin-exfoliating agent, a skin-tightening agent, a cosmeceutical agent, a vitamin, an anti-oxidant, a cell-signaling agent, a cell-modulating agent, a cell-interacting agent, a skin tanning agent, an anti-aging agent, an anti-wrinkle agent, a spot reducer, an alpha-hydroxy acid, a beta-hydroxy acid, a ceramide, or a combination thereof.

In one embodiment, the composition further comprises an agent, wherein the agent is a therapeutic agent. In one embodiment, the therapeutic agent is a nerve modulating agent, a pain-reliever, an analgesic, an anti-itching agent, an anti-irritant, a counterirritant, an immunomodulating agent, an immune system boosting agent, an immune system suppressing agent, anthralin, fluocinonide, methotrexate, cyclosporine, pimecrolimus, tacrolimus, azathioprine, fluoruracil, ceramide, an anti-acne agents (beta-hydroxy acid, a salicylic acid, benzoyl peroxide), an anti-flammatory agent, an antihistamine, a corticosteroid, a NSAIDs (Non-Steroidal Anti-Inflammatory Drugs), a blood-coagulating agent, an antineoplastic, a microbiome modulating agent, an antiseptic agent, an antibiotic, an anti-bacteria agent, an anti-fungal agent, an anti-viral agent, an anti-allergenic agent, a skin protection agent, a coal tar, an insect-repelling agent, a phototherapy agent, a magnetotherapy agent, a sonotherapy agent, a thermotherapy agent, a skin thermal regulating (cooling or heating) agent, or a combination thereof.

Provided herein is a kit for the formation of a film over the skin of a subject, wherein the kit comprises a) a first container comprising the composition of claim 1; and b) a second container comprising metal catalyst.

Provided herein is a method for delivering an agent to a subject, comprising in no particular order a) applying to said subject's skin the composition of claim 1; and b) applying to said subject's skin a metal catalyst; wherein said metal catalyst catalyzes an in situ polymerization of the bifunctional organopolysiloxane polymer, such that a film is formed on the skin, thereby delivering the agent to the subject; wherein the one or more agents is present in at least a) or b). In one embodiment, step (a) occurs before step (b). In one embodiment, step (a) occurs after step (b). In one embodiment, step (a) and step (b) occur concurrently. In one embodiment, the content of the first container and the content of the second container are pre-mixed and applied together.

Provided herein is a method for forming a film on the skin of a subject, comprising in no particular order a) applying to said subject's skin the composition of claim 1; and b) applying to said subject's skin a metal catalyst; wherein said metal catalyst catalyzes an in situ polymerization of the bifunctional organopolysiloxane polymer, such that a film is formed on the skin, thereby delivering the agent to the subject; wherein the one or more agents is present in at least a) or b). In one embodiment, step (a) occurs before step (b). In one embodiment, step (a) occurs after step (b). In one embodiment, step (a) and step (b) occur concurrently. In one embodiment, the content of the first container and the content of the second container are pre-mixed and applied together.

4 TERMINOLOGY, ABBREVIATIONS AND CONVENTIONS

As used herein, the term "skin" includes body surfaces where normal skin is intact, compromised, or partially or completely lost or removed. Skin further includes skin imperfections that are commonly considered to be part of "skin." Examples of skin imperfections include wrinkles, blemishes, freckles, acne, moles, warts, lesions, scars, tattoos, bruises, skin disfigurements, birth marks, sun damage, age damage, spots (e.g., aging spots), uneven skin tone, sagging skin, cellulite, stretch marks, loss of skin elasticity, skin roughness, enlarged pores, hyperpigmentation, telangiectasia, redness, shine, port wine stain (or nevus flammeus, e.g., nevus flammeus nuchae or midline nevus flammeus), and melasma. Skin further includes skin area over which any cosmetic, personal care, medical, paint, or any other foreign material, or a combination thereof, is applied.

As used herein, the term "layer" includes a covering, film, sheet, barrier, coating, membrane, device or prosthetic skin formed on, sprayed on, or spread over a surface. A layer may be, but is not necessarily, continuous. A layer may, but does not necessarily, have substantially even and/or uniform thickness.

As used herein, the terms "compromised skin barrier function," "compromised skin barrier," or "compromised skin condition" include conditions such as dermatological disorders, skin conditions, and wounds.

As used herein, the term "dermatological disorders" include disorders that cause at least one symptom on the skin of a subject that may require medical treatment. Dermatological disorders may be caused by, among other things, autoimmune disorders and/or environmental factors, such as allergens or chemicals. Examples of symptoms of dermatological disorders include, but are not limited to, itchy skin, dry skin, crusting, blistering, or cracking skin, dermatitis, skin edema, or skin lesion formation. Dermatological disorders include, but are not limited to, eczema, psoriasis, ichthyosis, rosacea, chronic dry skin, cutaneous lupus, lichen simplex chronicus, xeroderma, acne, disease-driven secondary dermatological disorder, and ulcer.

As used herein, eczema includes, e.g., atopic eczema, atopic dermatitis, contact dermatitis, phototoxic dermatitis, xerotic eczema (also known as asteatotic eczema, eczema craquele or craquelatum, winter itch, or pruritus hiemalis), seborrheic dermatitis (or seborrhoeic eczema), dyshidrosis (also known as dyshidrotic eczema, pompholyx, vesicular palmoplantar dermatitis, or housewife's eczema), discoid eczema (also known as nummular eczema, exudative eczema, microbial eczema), venous eczema (also known as gravitational eczema, stasis dermatitis, varicose eczema), dermatitis herpetiformis (also known as Duhring's Disease), neurodermatitis (also known as lichen simplex chronicus, localized scratch dermatitis), autoeczematization, and retinoid-induced dermatitis.

As used herein, psoriasis includes, e.g., psoriasis vulgaris (also known as plaque psoriasis), psoriatic erythroderma, pustular psoriasis (including von Zumbusch, Palmoplantar and Acropustulosis psoriasis), drug-induced psoriasis, inverse psoriasis, seborrheic-like psoriasis and guttate psoriasis.

As used herein, ichthyosis includes, e.g., ichthyosis vulgaris, acquired ichthyosis, X-linked ichthyosis, congenital ichthyosiform erythroderma, nonbullous (nbCIE), epidermolytic hyperkeratosis (bullous ichthyosis, bCIE), Harlequin type ichthyosis, ichthyosis bullosa of Siemens, ichthyosis hystrix, Curth-Macklin type, Hystrix-like ichthyosis with deafness, Lamellar ichthyosis, type 1, Lamellar ichthyosis, type 2, Lamellar ichthyosis, type 3, Lamellar ichthyosis, type 4, Lamellar ichthyosis, type 5, CHILD Syndrome, Conradi-Hünermann syndrome, ichthyosis follicularis with alopecia and photophobia syndrome, Keratitis-ichthyosis-deafness syndrome, Netherton syndrome, Neutral lipid storage disease with ichthyosis, adult Refsum disease, ichthyosis and male hypogonadism, Sjögren-Larsson syndrome, and photosensitive trichothiodystrophy (IBIDS syndrome).

As used herein, rosacea includes, e.g., erythematotelangiectatic rosacea, papulopustular rosacea, phymatous rosacea (e.g., rhinophyma), and granulomatous rosacea.

As used herein, cutaneous lupus includes, e.g., acute cutaneous lupus, subacute cutaneous lupus, chronic cutaneous lupus, chilblain lupus erythematosus, discoid lupus erythematosus, lupus erythematosus-lichen planus overlap syndrome, lupus erythematosus panniculitis, tumid lupus erythematosus and verrucous lupus erythematosus.

As used herein, acne includes, e.g., acne vulgaris, acne aestivalis, acne conglobate, acne cosmetic, acne fulminans, acne keloidalis nuchae, acne mechanica, acne medicamentosa (also known as drug-induced acne, e.g., steroid acne), acne miliaris necrotica, acne necrotica, acne rosacea, and hidradenitis suppurativa.

As used herein, the term "disease-driven secondary dermatological disorder" refers to a dermatological condition that may require treatment and was caused by or is associated with a non-dermatological disorder. A "non-dermatological disorder" includes disorders not primarily associated with the skin but which may result in, be associated with, or have a secondary manifestation of a skin condition, for example, a disorder of the circulatory system or metabolism of the subject. Disease-driven secondary dermatological disorders include, for example, an ulcer caused by diabetes mellitus (e.g., diabetic foot ulcer), a bacterial, viral or fungal infection, cancer, pressure (e.g., a bedsore), blood disorders, conditions affecting the nervous system (e.g., neuropathic ulcers (also known as "mal perforans")), conditions affecting the nervous system (e.g., arterial insufficiency ulcers (also known as "ischemic ulcers") or vascular ulcers), and/or a chronic wound.

As used herein, the term "skin conditions" include, but are not limited to, itchy skin, raw skin, dry skin, flaking or peeling skin, blisters on the skin, redness, swelling or inflammation of the skin, and oozing, scabbing or scaling skin. Skin conditions also include compromised skin barrier conditions caused by laser, light or chemical peel treatment.

As used herein, the term "wounds" include injuries to the skin wherein the skin is torn, cut or punctured. Wounds include open wounds, for example, abrasions, lacerations, incisions, punctures, avulsions, or amputations. Wounds also include burn wounds, a type of injury to skin and/or flesh caused by heat, electricity, wind, chemicals, light, radiation or friction.

As used herein, the terms "treat," "treating" and "treatment" include both therapeutic and prophylactic/preventative measures. "Treat," "treating" and "treatment" further include both disorder modifying treatment and symptomatic treatment. Treatment may ameliorate or cause a reduction in the severity and/or duration of at least one symptom of the conditions of compromised skin barrier function. Treatment may also cause a complete recovery from the conditions of compromised skin barrier function.

As used herein, the terms "apply," "applied" and "application" includes any and all known methods of contacting or administering compositions provided herein to a subject's skin or body. The application may be by finger, hand, brush, cotton ball, cotton swab, tissue, pad, sponge, roll-on, spatula, dispenser, drops, spray, splash, foam, mousse, serum, spritz, and other appropriate methods.

As used herein, the term "subject" includes subjects in which the compositions disclosed herein would be appropriate for use, particularly animals (e.g., a human). Subjects may further include plants, wherein skin refers to the surface over portions of the plant that may benefit from application of the composition, such as flowers, leaves, fruits, stems, branches, bark, and roots.

As used herein, the term "In vitro" means tested or formed not on, in, or over a subject's skin or body.

As used herein, the term "routine daily activities" includes instrumental activities of daily living, such as feeding (e.g., eating, drinking, taking medications), continence (e.g., urination and defecation), toileting, dressing, bathing (e.g., shower, bath), grooming, physical ambulation (e.g., walking, using transportation), talking (e.g., using the telephone), preparing food, housekeeping, doing laundry, shopping, and handling finances. Examples of such daily activities are described in Lawton and Brody, Assessment of older people: self-maintaining and instrumental activities of daily living, *Gerontologist* 1969 Autumn; 9(3):179-86 and Katz et al., Studies of Illness in the Aged. The Index of ADL: A Standardized Measure of Biological and Psychosocial Function, *JAMA* 1963 Sep. 21; 185:914-9.

As used herein, the term "demanding activities" includes activities that generate elevated level of strain and/or stress on the skin of a subject as compared to the strain or stress generated by routine daily activities. Examples of such demanding activities include exercising, swimming (in seawater, fresh water or chlorinated water), steam room (heat at high humidity), sauna (heat at low humidity), and other like activities.

Unless otherwise stated, descriptions of any material used as part of any composition disclosed herein are of such material as an ingredient of the composition prior to mixing, combination and/or reaction of such material with other ingredient(s) of the composition.

As used herein, the term "crosslinkable polymer" refers to a polymer that can physically or chemically interact, or both physically and chemically interact, with itself or with other polymers to form a layer on a surface (e.g., skin, leather, glass, plastic, metal) to which it is applied. "Physically interact" refers to the formation of non-covalent interaction (e.g., hydrogen bonds, or electrostatic, polar, ionic, van der Waals, or London forces) between two or more polymer chains. "Chemically interact" refers to the formation of covalent bonds between two or more polymer chains. Covalent bonds may be formed through chemical reactions that occur spontaneously or are initiated by, for example, catalyst, moisture, heat, pressure, change in pH, or radiation. The crosslinkable polymer(s) may be homopolymer or copolymer, for example, random copolymer, alternating copolymer, periodic copolymer, statistical copolymer, block copolymer, graft or grafted copolymer, or a combination thereof. In one embodiment, the crosslinkable polymer is polyglycerin. In one embodiment, the crosslinkable polymer is KSG-710. In one embodiment, the crosslinkable polymer is KSG-710 supplied by Shin-Etsu.

In preferred embodiments, the composition comprises one or more organopolymer(s). An "organopolymer" refers to a polymer that includes carbon. In preferred embodiments, the organopolymer is a bifunctional organopolysiloxane polymer. In preferred embodiments, the bifunctional organopolysiloxane polymer is a linear siloxane polymer. In preferred embodiments, the bifunctional organopolysiloxane polymer is a branched siloxane polymer.

The term "viscosity" refers to the measure of the resistance of a fluid which is being deformed by either shear stress or tensile stress. The viscosity of the composition affects the thickness, spreadability, and evenness and/or uniformity of the layer formed on a substrate. Viscosity may be reported as either dynamic viscosity (also known as absolute viscosity, typical units Pa·s, Poise, P, cP) or kinematic viscosity (typical units $cm^2/s$, Stokes, St, cSt), which is the dynamic viscosity divided by density of the fluid measured. Viscosity ranges of the ingredients disclosed herein are commonly provided by the supplier of the ingredients in units of kinematic viscosity (e.g., cSt), as measured using a Rheometer or a Cannon-Fenske Tube Viscometer.

Viscosity of a fluid can be measured in vitro, for example, using a rheometer (e.g., linear shear rheometer or dynamic shear rheometer) or a viscometer (also called viscosimeter, e.g., capillary viscometer or rotational viscometer), at an instrument specific strain. For example, Thomas G. Mezger, The Rheology Handbook: For Users of Rotational and Oscillatory Rheometers (2nd Ed.), Vincentz Network, 2006, and American Society for Testing and Materials (ASTM) standards such as ASTM D3835-08, ASTM D2857-95, ASTM D2196-10, and ASTM D2983-09 provide instructions on how to measure the viscosity of a fluid. Viscosity of a fluid is preferably measured in vitro using the Rheometer Viscosity Measurement Test described herein. Density of the fluid may vary with temperature or pressure. Unless otherwise specified, all properties of compositions, layers and/or devices disclosed herein, including viscosity, are measured at room temperature (about 25° C.) and about 1 atmosphere air pressure.

Anhydrous compositions generally have longer shelf-life than emulsions with similar ingredients, without the need for preservatives against bacteria or mold. "Anhydrous" as used herein refers to containing as an ingredient less than about 10%, less than about 5%, less than about 2%, less than about 1%, or less than about 0.1% water. In some embodiments, the composition is anhydrous. In some embodiments, the composition is an emulsion. In some embodiments, the composition is a dispersion. In some embodiments, the composition is a suspension. In some embodiments, the composition is a paste. In some embodiments, the composition is a semi-solid. In some embodiments, the composition is an ointment. In some embodiments, the composition is a cream. In some embodiments, the composition is a serum. In some embodiments, the composition is a lotion. In some embodiments, the composition is a patch. In certain embodiments, the composition can be spread, sprayed, stenciled stamped, patterned, patched, transferred, layered, covered or spritzed over skin.

The term "glass transition temperature" refers to the temperature at a transition from the solid state to the liquid state occurs. A glass transition temperature may be reported as a temperature (° C., ° F. or K). Glass transition temperature can be measured in vitro, for example, using thermal analysis instruments such as a Differential Scanning Calorimeter (DSC) or a Thermogravimetric Analysis (TGA).

The term "tack-free time" refers to the time when the layer has solidified sufficiently that it no longer sticks to a finger or a substrate that lightly touches it under normal force less than 0.15 Newtons, incurring stickiness to the film.

The term "adhesive force" refers to the force per unit length required to separate the materials adhered to a standard substrate such as leather or polypropylene or polyurethane. In certain embodiments, the adhesive force of the layer on polypropylene substrate is greater than about 2 N/m.

The terms "tensile strength," or "ultimate tensile strength," or "fracture stress," or "stress at break," or "maximum tensile stress," or "ultimate tensile stress," or "fracture strength," or "breaking strength" refer to stress at which a specimen fails via fracture. Tensile strength can be measured on a specimen formed from the composition in vitro, for example, using the Cyclic and Extension Pull Test as described herein.

The terms "fracture strain," or "elongation at break," or "stretchiness at break," or "strain at break," or "maximum elongation," or "maximum strain," or "maximum stretchiness" or "extension at break" or "maximum extension" refer to strain at which a specimen fails via fracture. Fracture strain can be measured on a specimen formed from the composition in vitro, for example, using the Cyclic and Extension Pull Test as described herein.

The terms "tensile modulus," or "Young's modulus," or "modulus of elasticity," or "stiffness," or "tensile stiffness," or "elastic modulus" refer to the force per unit area that is needed to stretch and deform a material beyond the initial length. Tensile modulus is an inverse of compliance, relating to flexibility or deformability of a material beyond the initial length. Tensile modulus can be measured on a specimen formed from the composition in vitro, for example, using the Cyclic and Extension Pull Test as described herein. Tensile modulus can also be measured using the ASTM D5083 Tensile Properties of Reinforced Thermosetting Plastics Using Straight-Sided Specimens standard test.

The terms "shear modulus" or "modulus of rigidity" or "shear stiffness" refer to the force per unit area that is needed to shear and deform a material beyond the initial length. Shear modulus is be measured on a specimen formed from the composition in vitro by using the ASTM D7175 Determining the Rheological Properties of Asphalt Binder using a Dynamic Shear Rheometer.

The term "cyclic tensile residual strain" refers to tensile residual strain after cyclic tensile deformation. The term "residual strain" refers to strain that remains in a material after the original cause of stress has been removed. Residual strain may be reported as plastic strain, inelastic strain, non-elastic strain, or viscoelastic strain. The cyclic tensile residual strain can be measured on a specimen formed from the composition in vitro, for example, using the Cyclic and Extension Pull Test as described herein.

The terms "cyclic tensile hysteresis loss energy" or "cyclic hysteresis strain energy" refer to the excess energy being dissipated as heat when the specimen is subjected to cyclic tensile deformation. Cyclic tensile hysteresis loss energy can be measured on a specimen formed from the composition in vitro, for example, using the Cyclic and Extension Pull Test as described herein.

The terms "fracture toughness," or "toughness," or "tensile toughness," or "deformation energy," or "failure energy," or "fracture energy" refer to the ability to absorb energy of mechanical deformation per unit volume up to the point of failure. Fracture toughness can be measured on a specimen formed from the composition in vitro, for example, using the Cyclic and Extension Pull Test as described herein.

The term "oxygen transmission rate" or OTR refers to the permeation flux of oxygen through a membrane with certain thickness. Oxygen transmission rate can be measured on a specimen formed from the composition in vitro, for example, using the ASTM F2622 Oxygen Gas Transmission Rate Through Plastic Film and Sheeting Using Various Sensors test.

The term "oxygen permeance" refers to the permeation flux of oxygen through a membrane with certain thickness, per unit oxygen vapor pressure difference between the membrane (typically in cmHg). Oxygen permeance can be measured on a specimen formed from the composition in vitro, for example, using the ASTM F2622 Oxygen Gas Transmission Rate Through Plastic Film and Sheeting Using Various Sensors test.

The terms "oxygen permeability coefficient" or "intrinsic oxygen permeability" refer to a measure of how fast the oxygen can move through a membrane, which involves a successive process of oxygen sorption into a membrane then followed by oxygen diffusion through the membrane. Oxygen permeability coefficient can be measured on a specimen formed from the composition in vitro, for example, using the ASTM F2622 Oxygen Gas Transmission Rate Through Plastic Film and Sheeting Using Various Sensors test.

The term "water vapor transmission rate" or WVTR refers to the permeation flux of water vapor through a membrane with certain thickness. Water vapor transmission rate can be measured on a specimen formed from the composition in vitro, for example, using the ASTM F1249 Water Vapor Transmission Rate Through Plastic Film and Sheeting Using a Modulated Infrared Sensor test.

The term "water vapor permeance" refers to the permeation flux of water vapor through a barrier with certain thickness, per unit water vapor pressure difference between one side and the other side of the barrier (typically in cmHg). Water vapor permeance can be measured on a specimen formed from the composition in vitro, for example, using the ASTM F1249 Water Vapor Transmission Rate Through Plastic Film and Sheeting Using a Modulated Infrared Sensor test.

The terms "water vapor permeability coefficient" or "intrinsic water vapor permeability" refer to a measure of how fast water vapor can move through a barrier, which involves a successive process of water vapor sorption into a barrier, followed by water vapor diffusion through the barrier. Water vapor permeability coefficient can be measured on a specimen formed from the composition in vitro, for example, using the ASTM F1249 Water Vapor Transmission Rate Through Plastic Film and Sheeting Using a Modulated Infrared Sensor test.

The term "transepidermal water loss" refers to the measurement of the quantity of water that passes from inside a body through the epidermal layer to the surrounding atmosphere via diffusion and evaporation processes. Transepidermal water loss is measured by using the Transepidermal Water Loss (TEWL) Measurement Test as described herein. Differences in TEWL measurements caused by age, race, gender, and/or area of the skin of the subject tested are generally less than the standard error in the TEWL measurements.

The term "skin hydration" refers to the measure of water content of the skin, typically through a Corneometer which is based on capacitance measurement of a dielectric medium near skin surface.

The term "retraction time" refers to the time taken for the skin to return to its original state after initial deformation by the Suction Cup device. Skin retraction time can be measured, for example, using a cutometer/suction cup pursuant to the procedure as described in H. Dobrev, "Use of Cutometer to assess epidermal hydration," *Skin Research and Technology* 2000, 6(4):239-244.

5 DETAILED DESCRIPTION

Provided herein are compositions that results in a film over the skin of the subject with the properties described herein. In certain embodiments, the film can be used for cosmetic and therapeutic applications.

5.1 Compositions for Use with the Methods Provided Herein

In certain embodiments, provided herein are compositions for the formation of a layer over the skin of a subject, comprising a) a bifunctional organopolysiloxane polymer having one unsaturated group and one hydride group; and b) a reinforcing constituent suitable for formation of a film on the subject's skin. In certain embodiments, the bifunctional organopolysiloxane polymer is a linear siloxane polymer. In certain embodiments, the bifunctional organopolysiloxane polymer is a branched siloxane polymer.

In certain embodiments, the unsaturated group is not particularly limited, and may be, for example, a vinyl, styryl, allyl, methallyl, hexenyl, octenyl or alkynyl group. The preferred unsaturated group is a vinyl group.

In certain embodiments, the unsaturated group or the hydride group are terminal groups.

In certain embodiments, the siloxane polymer has a degree of polymerization of at least 20 and a dispersity index less than about 1.2, and wherein a ratio of unsaturated terminal groups to hydride terminal groups is substantially 1:1. In certain embodiments, the degree of polymerization is about 20 to about 200. In certain embodiments, the unsaturated terminal group is selected from the group consisting of vinyl, styryl, allyl, methallyl, hexenyl, octenyl and alkynyl. In certain embodiments, the siloxane backbone is selected from the group consisting of diphenylsiloxane, phenylmethylsiloxane, trifluoropropylmethylsiloxane, dimethylsilylethylsiloxane, and alkylmethylsiloxane. In certain embodiments, the siloxane backbone is dimethylsiloxane and the unsaturated group is vinyl. In certain embodiments, the film has no apparent crosslinking. In certain embodiments, the linear siloxane polymer is a monovinyl-monohydride terminated polysiloxane. In certain embodiments, the film is formed via hydrosilylation step-growth polymerization of the linear siloxane polymer. In certain embodiments, the linear siloxane polymer is capable of being reacted with a metal catalyst to form the film over the subject's skin. In certain embodiments, the linear siloxane polymer is compounded with the reinforcing constituent prior to the reaction with the metal catalyst. In certain embodiments, the metal catalyst is a platinum catalyst. In certain embodiments, the reinforcing constituent is fumed silica. In certain embodiments, the linear siloxane polymer is a monovinyl-monohydride terminated polydimethylsiloxane.

In certain embodiments, the composition is a two-part composition, e.g., the first part and the second part. In certain embodiments, the first part and the second part are applied either one at a time or in combination to form the layer. In certain embodiments, the first part comprises a bifunctional organopolysiloxane polymer as described herein. In certain embodiments, the first part further comprises an organopolysiloxane with at least two alkenyl functional groups or at least one alkynyl functional group, either at the terminal or at the side chain or both, as shown in formula (I):

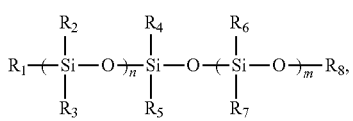

wherein at least two of $R_1$, $R_4$, $R_5$ and $R_8$ are alkenyl groups or at least one of $R_1$, $R_4$, $R_5$ and $R_8$ is alkynyl group;
the rest of $R_1$, $R_4$, $R_5$ and $R_8$ are $C_{1-20}$ alkyl groups;
$R_2$, $R_3$, $R_6$ and $R_7$ are $C_{1-20}$ alkyl groups; and
the sum of n and m is between 2 to 1,000,000.

In certain embodiments, the first part further comprises an organopolysiloxane with at least two hydride functional groups, either at the terminal or at the side chain or both, as shown in formula (II):

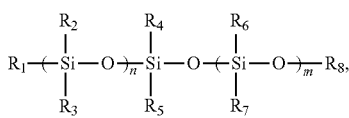

wherein at least two of $R_1$, $R_4$, $R_5$ and $R_8$ are hydride groups;
the rest of $R_1$, $R_4$, $R_5$ and $R_8$ are $C_{1-20}$ alkyl groups;
$R_2$, $R_3$, $R_6$ and $R_7$ are $C_{1-20}$ alkyl groups; and
the sum of n and m is between 2 to 1,000,000.

In certain embodiments, the first part further comprises an organopolysiloxane with at least one alkenyl functional group or at least one alkynyl functional group; and at least one hydride functional group, either at the terminal or at the side chain or both, as shown in formula (III):

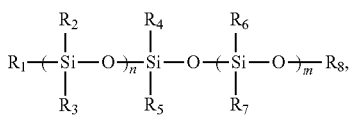

wherein at least one of $R_1$, $R_4$, $R_5$ and $R_8$ is an alkenyl functional group or at least one of $R_1$, $R_4$, $R_5$ and $R_8$ is alkynyl group; and at least one of $R_1$, $R_4$, $R_5$ and $R_8$ is a hydride group;
the rest of $R_1$, $R_4$, $R_5$ and $R_8$ are $C_{1-20}$ alkyl groups;
$R_2$, $R_3$, $R_6$ and $R_7$ are $C_{1-20}$ alkyl groups; and
the sum of n and m is between 2 to 1,000,000.

In certain embodiments, the first part further comprises a reinforcing constituent. In certain embodiments, the first part further comprises a reinforcing constituent selected from the group consisting of optionally surface treated mica, zinc oxide, titanium dioxide, aluminum oxide, clay or silica.

In certain embodiments, the first part further comprises an agent, wherein the agent is anti-oxidants, vitamins, vitamin D3 analogues, retinoids, minerals, mineral oil, petroleum jelly, fatty acids, plant extracts, polypeptides, antibodies, proteins, sugars, humectants, emollients, or a combination thereof. In certain embodiments, the first part further comprises a cosmetic agent. In certain embodiments, the first part further comprises a cosmetic agent selected from a moisturizer, a sunscreen, a UV protecting agent, a skin-protectant agent, a skin-soothing agent, a skin-lightening agent, a skin-brightening agent, a skin-softening agent, a skin-smoothening agent, a skin-bleaching agent, a skin-exfoliating agent, a skin-tightening agent, a cosmeceutical agent, a vitamin, an anti-oxidant, a cell-signaling agent, a cell-modulating agent, a cell-interacting agent, a skin tanning agent, an anti-aging agent, an anti-wrinkle agent, a spot reducer, an alpha-hydroxy acid, a beta-hydroxy acid, a ceramide, or a combination thereof. In certain embodiments, the first part further comprises a therapeutic agent. In certain embodiments, the first part further comprises a therapeutic agent selected from a nerve modulating agent, a pain-reliever, an analgesic, an anti-itching agent, an anti-irritant, a counterirritant, an immunomodulating agent, an immune system boosting agent, an immune system suppressing agent, anthralin, fluocinonide, methotrexate, cyclosporine, pimecrolimus, tacrolimus, azathioprine, fluoruracil, ceramide, an anti-acne agents (beta-hydroxy acid, a salicylic acid, benzoyl peroxide), an anti-flammatory agent, an anti-histamine, a corticosteroid, a NSAIDs (Non-Steroidal Anti-Inflammatory Drugs), a blood-coagulating agent, an antineoplastic, a microbiome modulating agent, an anti-septic agent, an antibiotic, an anti-bacteria agent, an anti-fungal agent, an anti-viral agent, an anti-allergenic agent, a skin protection agent, a coal tar, an insect-repelling agent, a phototherapy agent, a magnetotherapy agent, a sonotherapy agent, a thermotherapy agent, a skin thermal regulating (cooling or heating) agent, or a combination thereof.

In certain embodiments, the second part comprises a catalyst that is capable of catalyzing the formation of a film on the subject's skin. In certain embodiments, the second part comprises a metal catalyst. In certain embodiments, the second part comprises a platinum catalyst.

In certain embodiments, the second part further comprises an organopolysiloxane with at least two alkenyl functional groups, either at the terminal or at the side chain or both as shown in formula (I) herein. In certain embodiments, the second part further comprises an agent, wherein the agent is anti-oxidants, vitamins, vitamin D3 analogues, retinoids, minerals, mineral oil, petroleum jelly, fatty acids, plant extracts, polypeptides, antibodies, proteins, sugars, humectants, emollients, or a combination thereof. In certain embodiments, the second part further comprises a cosmetic agent. In certain embodiments, the second part further comprises a cosmetic agent selected from a moisturizer, a sunscreen, a UV protecting agent, a skin-protectant agent, a skin-soothing agent, a skin-lightening agent, a skin-brightening agent, a skin-softening agent, a skin-smoothening agent, a skin-bleaching agent, a skin-exfoliating agent, a skin-tightening agent, a cosmeceutical agent, a vitamin, an anti-oxidant, a cell-signaling agent, a cell-modulating agent, a cell-interacting agent, a skin tanning agent, an anti-aging agent, an anti-wrinkle agent, a spot reducer, an alpha-hydroxy acid, a beta-hydroxy acid, a ceramide, or a combination thereof. In certain embodiments, the second part further comprises a therapeutic agent. In certain embodiments, the second part further comprises a therapeutic agent selected from a nerve modulating agent, a pain-reliever, an analgesic, an anti-itching agent, an anti-irritant, a counter-irritant, an immunomodulating agent, an immune system boosting agent, an immune system suppressing agent, anthralin, fluocinonide, methotrexate, cyclosporine, pimecrolimus, tacrolimus, azathioprine, fluoruracil, ceramide, an anti-acne agents (beta-hydroxy acid, a salicylic acid, benzoyl peroxide), an anti-flammatory agent, an antihistamine, a corticosteroid, a NSAIDs (Non-Steroidal Anti-Inflammatory Drugs), a blood-coagulating agent, an antineoplastic, a microbiome modulating agent, an anti-septic agent, an antibiotic, an anti-bacteria agent, an anti-fungal agent, an anti-viral agent, an anti-allergenic agent, a skin protection agent, a coal tar, an insect-repelling agent, a phototherapy agent, a magnetotherapy agent, a sonotherapy agent, a thermotherapy agent, a skin thermal regulating (cooling or heating) agent, or a combination thereof.

In certain embodiments, the first part has a viscosity above about 1 cP, above about 10 cP, above about 100 cP, above about 500 cP, or above about 1000 cP at about 25° C. In preferred embodiments, the first part has a viscosity above about 2000 cP, above about 5000 cP at about 25° C. In further preferred embodiments, the first part has a viscosity above about 15,000 cP at about 25° C. In certain embodiments, the first part has a viscosity below about 1,000,000 cP, below about 750,000 cP, below about 500,000 cP, or below about 250,000 cP at about 25° C. In preferred embodiments, the first part has a viscosity below about 200,000 cP, below about 175,000 cP, below about 150,000 cP, below about 125,000 cP, below about 100,000 cP, or below about 50,000 cP, or below 25,000 cP at about 25° C.

In certain embodiments, the second part has a viscosity above about 1 cP, above about 10 cP, above about 100 cP, above about 500 cP, or above about 1000 cP at about 25° C. In preferred embodiments, the first part has a viscosity above about 2000 cP, above about 5000 cP at about 25° C. In further preferred embodiments, the first part has a viscosity above about 15,000 cP at about 25° C. In certain embodiments, the first part has a viscosity below about 1,000,000 cP, below about 750,000 cP, below about 500,000 cP, or below about 250,000 cP at about 25° C. In preferred embodiments, the first part has a viscosity below about 200,000 cP, below about 175,000 cP, below about 150,000 cP, below about 125,000 cP, below about 100,000 cP, or below about 50,000 cP, or below 25,000 cP at about 25° C.

Another aspect provided herein is directed to a composition that forms a layer that does not significantly change the shine and/or gloss of the area over which the composition is applied. Shine and/or gloss can be measured on a specimen formed from the composition in vitro, for example, using a Glossmeter pursuant to the ASTM D523 Specular Gloss test, at 20°, 60°, and/or 85° measurement angles. The light and measurement angel can be selected based on the anticipated gloss range. For example, if the measurement made at 60° is greater than about 70 gloss units (GU), the measurement angle should be changed to 20° to optimize measurement accuracy. Conversely, if the measurement made at 60° is less than about 10 GU, the measurement angle should be changed to 85° to optimize measurement accuracy. 45° or 75° measurement angle may also be used depending on the gloss of the substrate used for the test. Various materials can be used as substrate to mimic normal, healthy skin for the test, for example, Cowhide Tooling leather in natural color. Shine and/or gloss change is indicated by the percentage increase or decrease of gloss units in a measurement area after the treatment comparing to before treatment. In certain embodiments, the shine and/or gloss change of the area treated with the composition is less than about 20%. In preferred embodiments, the shine and/or gloss change of the area treated with the composition is less than about 10%. In further preferred embodiments, the shine and/or gloss change of the area treated with the composition is less than about 5%.

In certain embodiments, the average thickness of the layer is less than about 0.5 mm (500 microns). In preferred embodiments, the average thickness of the layer is about 0.5 to about 500 microns, about 1 to about 250 microns, about 10 to about 100 microns, about 30 to about 70 microns, about 40 to about 60 microns. In further preferred embodiments, the average thickness of the layer is about 50 microns.

In certain embodiments, the composition that forms the layer has a glass transition temperature below about 37° C. In preferred embodiments, the composition that forms the layer has a glass transition temperature below about 25° C. In further preferred embodiments, the composition that forms the layer has a glass transition temperature below about 0° C. In certain embodiments, the first part of the composition that forms the layer has a glass transition temperature below about 37° C. In preferred embodiments, the first part of the composition that forms the layer has a glass transition temperature below about 25° C. In further preferred embodiments, the first part of the composition that forms the layer has a glass transition temperature below about 0° C. In certain embodiments, the second part of the composition that forms the layer has a glass transition temperature below about 37° C. In preferred embodiments, the second part of the composition that forms the layer has a glass transition temperature below about 25° C. In further preferred embodiments, the second part of the composition that forms the layer has a glass transition temperature below about 0° C.

In certain embodiments, the composition has a set-to-touch time of greater than about 1 second and less than about 10 minutes. In preferred embodiments, the composition has a set-to-touch time of greater than about 30 seconds and less than about 4 minutes. In further preferred embodiments, the composition has a set-to-touch time of greater than about 30 seconds and less than about 2 minutes. In further preferred embodiments, the composition has a set-to-touch time of greater than about 1 minute and less than about 2 minutes. In other preferred embodiments, the composition has a set-to-touch time of about 1.5 minutes. Polyurethane and polypropylene have surface conditions preferably used for the measurement of set-to-touch time due to its smoothness, and low aspect ratio and cure characters in-vitro that are similar to the cure characters on skin in-vivo.

In certain embodiments, the composition has a tack-free time of greater than about 1 second and less than about 10 minutes. In preferred embodiments, the composition has a tack-free time of greater than about 30 seconds and less than about 4 minutes. In further preferred embodiments, the composition has a tack-free time of greater than about 30 seconds and less than about 2 minutes. In further preferred embodiments, the composition has a tack-free time of greater than about 1 minute and less than about 2 minutes. In other preferred embodiments, the composition has a tack-free time of about 1.5 minutes. Polyurethane and polypropylene have surface conditions preferably used for the measurement of tack-free time due to their smooth surface with low aspect ratio and cure characters in-vitro that are similar to the cure characters on skin in-vivo.

In certain embodiments, the layer remains substantially intact on the skin for about 24 hours or more with common, routine daily activities and/or with demanding activities. In preferred embodiments, the layer remains substantially intact on the skin for at least about 30 hours, about 36 hours, about 48 hours, about 60 hours, about 72 hours, about 84 hours, or about 96 hours with common, routine daily activities and/or with demanding activities. In other preferred embodiments, the layer remains substantially intact on the skin for at least about 120 hours, about 144 hours, or about 168 hours with common, routine daily activities and/or with demanding activities. "Remain substantially intact" means that the layer remains on at least about 50%, at least about 60%, at least about 70%, at least about 80%, at least about 90%, at least about 95% of the area of the skin to which it was originally applied, or at least about 50%, at least about 60%, at least about 70%, at least about 80%, at least about 90%, at least about 95% by weight remains on the skin.

In certain embodiments, the layer remains at least about 50% intact, at least about 60% intact, at least about 70% intact by either area or by weight on the skin for about 24 hours or more with common, routine daily activities and/or with demanding activities. In preferred embodiments, the layer remains at least about 80% intact by either area or by weight on the skin for about 24 hours or more with common, routine daily activities and/or with demanding activities. In other preferred embodiments, the layer remains at least about 90% intact, or at least about 95% intact by either area or by weight on the skin for about 24 hours or more with common, routine daily activities and/or with demanding activities. In certain embodiments, the layer remains at least about 50% intact, at least about 60% intact, at least about 70% intact by either area or by weight on the skin for at least about 30 hours, about 36 hours, about 48 hours, about 60 hours, about 72 hours, about 84 hours, about 96 hours, at least about 120 hours, about 144 hours, or about 168 hours with common, routine daily activities and/or with demanding activities. In preferred embodiments, the layer remains at least about 80% intact by either area or by weight on the skin for at least about 30 hours, about 36 hours, about 48 hours, about 60 hours, about 72 hours, about 84 hours, about 96 hours, at least about 120 hours, about 144 hours, or about 168 hours with common, routine daily activities and/or with demanding activities. In other preferred embodiments, the layer remains at least about 90% intact, or at least about 95% intact by either area or by weight on the skin for at least about 30 hours, about 36 hours, about 48 hours, about 60 hours, about 72 hours, about 84 hours, about 96 hours, at least about 120 hours, about 144 hours, or about 168 hours with common, routine daily activities and/or with demanding activities.

Another aspect provided herein is directed to a composition that forms a layer on the skin that resists peeling. Resistance to peeling is determined by measuring adhesive force using the Peel Adhesion test described herein. In preferred embodiment, the adhesive force of the layer on polypropylene substrate is greater than about is greater than about 5 N/m. In further preferred embodiments, the adhesive force of the layer on polypropylene substrate is greater than about 20 N/m, 40 N/m, 60 N/m, 80 N/m, greater than about 100 N/m, or greater than about 200 N/m.

Another aspect provided herein is directed to a composition that forms a layer that is resistant to environmental factors, such as exposure to heat, cold, wind, water, humidity, bodily fluids (e.g., blood, pus/liquor puris, urine, saliva, sputum, tears, semen, milk, or vaginal secretion), sebum, saline, seawater, soapy water, detergent water, or chlorinated water. Such resistance to environmental factors is represented by the minimal weight increase upon exposures to these environmental factors. The weight change of the layer is determined by using the ASTM D2765-95 Determination of Gel Content and Swell Ratio of Crosslinked Ethylene Plastics test using a weight scale. In certain embodiments, the weight of the layer increases by less than about 10% upon exposure to such environmental factors at about 1-hour time point (i.e., 1 hour after application of the composition disclosed herein), about 4-hour, about 6-hour, about 12-hour, about 24-hour, about 30-hour, about 36-hour, about 48-hour, or between 48 hours and one week time point. In preferred embodiments, the weight of the layer increases by less than about 5%, or less than about 1% upon exposure to such environmental factors at about 1-hour, about 4-hour, about 6-hour, about 12-hour, about 24-hour, about 30-hour, about 36-hour, about 48-hour, or between 48 hours and one week time point. In further preferred embodiments, the weight of the layer increases by less than about 0.5% upon exposure to such environmental factors at about 1-hour, about 4-hour, about 6-hour, about 12-hour, about 24-hour, about 30-hour, about 36-hour, about 48-hour, or between 48 hours and one week time point.

In certain embodiments, the weight of the layer increases by less than about 50% upon exposure to such environmental factors at about 1-hour time point (i.e., 1 hour after application of the composition disclosed herein), about 4-hour, about 6-hour, about 12-hour, about 24-hour, about 30-hour, about 36-hour, about 48-hour, or between 48-hour and one-week time point. In preferred embodiments, the weight of the layer increases by less than about 5%, or less than about 1% upon exposure to such environmental factors at about 1-hour, about 4-hour, about 6-hour, about 12-hour, about 24-hour, about 30-hour, about 36-hour, about 48-hour, or between 48-hour and one-week time point. In further preferred embodiments, the weight of the layer increases by less than about 0.5% upon exposure to such environmental factors at about 1-hour, about 4-hour, about 6-hour, about 12-hour, about 24-hour, about 30-hour, about 36-hour, about 48-hour, or between 48-hour and one-week time point.

Another aspect provided herein is directed to a composition that forms a layer that is flexible, stretchable, elastic and body-movement conforming. Such flexible, stretchable, elastic and body-movement conforming properties of the layer are represented by the tensile modulus, shear modulus, cyclic tensile residual strain, cyclic tensile hysteresis loss energy, fracture strain, fracture stress, and fracture toughness measurements, which can be tested in vitro on a specimen formed from the composition using the methods described herein. For a layer to have the appearance and durability of normal, healthy skin, these physical properties of the layer preferably fall within specific ranges so that the layer will not break when being deformed by body movements and will return to essentially the same state when the body returns to the original state.

In certain embodiments, the tensile strength of the layer is greater than about 0.05 MPa, or greater than 0.10 MPa, or greater than 0.20 MPa, or greater than about 0.5 MPa. In preferred embodiments, the tensile strength of the layer is greater than about 1.0 MPa, or greater than about 2.0 MPa. In preferred embodiments, the tensile strength of the layer is less than about 5 MPa. In further preferred embodiments, the tensile strength of the layer is about 3.0 MPa.

In certain embodiments, the fracture strain of the layer is greater than about 25%, greater than 50%, greater than about 100%, greater than about 200%, or greater than about 400%. In further preferred embodiments, the fracture strain of the layer is greater than about 600%, greater than about 800%, greater than about 1000%, greater than about 1200, or greater than about 1500%.

In certain embodiments, the tensile modulus of the layer is about 0.01 to about 40 MPa. In preferred embodiments, the tensile modulus of the layer is about 0.05 to about 20 MPa, or about 0.1 to about 10 MPa, about 0.1 to about 5 MPa, about 0.1 to about 1 MPa. In further preferred embodiments, the tensile modulus of the layer is about 0.25 to about 0.75 MPa. In further preferred embodiments, the tensile modulus of the layer is about 0.5 MPa.

In certain embodiments, the shear modulus of the layer is about 0.005 to about 10 MPa. In preferred embodiments, the shear modulus of the layer is about 0.05 to about 5 MPa, or about 0.1 to about 1 MPa. In further preferred embodiments, the shear modulus of the layer is about 0.25 to about 0.75 MPa. In further preferred embodiments, the shear modulus of the layer is about 0.5 MPa.

In certain embodiments, the cyclic tensile residual strain of the layer is less than about 10%. In preferred embodiments, the cyclic tensile residual strain of the layer is less than about 5% or less than about 2.5%. In further preferred embodiments, the cyclic tensile residual strain of the layer is less than about 1%. In other preferred embodiments, the cyclic tensile residual strain of the layer is less than about 0.5%, less than about 0.25%, or less than about 0.1%.

In certain embodiments, the cyclic tensile hysteresis loss energy of the layer is less than about 1 $kJ/m^3$. In preferred embodiments, the cyclic tensile hysteresis loss energy of the layer is less than about 0.5 $kJ/m^3$. In further preferred embodiments, the cyclic tensile hysteresis loss energy of the layer is less than about 0.2 $kJ/m^3$.

In certain embodiments, the fracture toughness of the layer is greater than about 500 $kJ/m^3$. In preferred embodiments, the fracture toughness of the layer is greater than about 5,000 $kJ/m^3$. In further preferred embodiments, the fracture toughness of the layer is greater than about 10,000 $kJ/m^3$, or greater than about 50,000 $kJ/m^3$.

Another aspect provided herein is directed to a composition that forms a layer that is permeable to oxygen and water vapor, as represented by the oxygen permeability coefficient, water vapor permeability coefficient, oxygen transmission rate, water vapor transmission rate, oxygen permeance and/or water vapor permeance, which are tested in vitro using the methods described herein.

In certain embodiments, the oxygen transmission rate of the layer is greater than about $5\times10^{-9}$ $cm^3/(cm^2 \cdot s)$. In preferred embodiments, the oxygen transmission rate of the layer is greater than about $5\times10^4$ $cm^3/(cm^2 \cdot s)$. In further preferred embodiments, the oxygen transmission rate of the layer is greater than about $5\times10^{-5}$ $cm^3/(cm^2 \cdot s)$. In other preferred embodiments, the oxygen transmission rate of the layer is greater than about $5\times10^{-4}$ $cm^3/(cm^2 \cdot s)$, greater than about $5\times10^{-3}$ $cm^3/(cm^2 \cdot s)$, greater than about $5\times10^{-2}$ $cm^3/(cm^2 \cdot s)$, greater than about 0.5 $cm^3/(cm^2 \cdot s)$. In preferred embodiments, the oxygen transmission rate of the layer is less than about 5 $cm^3/(cm^2 \cdot s)$.

In certain embodiments, the oxygen permeance of the layer is greater than about $5\times10^{-11}$ $cm^3/(cm^2 \cdot s \cdot cm\ Hg)$. In preferred embodiments, the oxygen permeance of the layer is greater than about $5\times10^{-9}$ $cm^3/(cm^2 \cdot s \cdot cm\ Hg)$, or greater than about $5\times10^7$ $cm^3/(cm^2 \cdot s \cdot cm\ Hg)$. In further preferred embodiments, the oxygen permeance of the layer is greater than about $5\times10^{-6}$ $cm^3/(cm^2 \cdot s \cdot cm\ Hg)$. In other preferred embodiments, the oxygen permeance of the layer is greater than about $5\times10^{-5}$ $cm^3/(cm^2 \cdot s \cdot cm\ Hg)$, greater than about $5\times10^{-4}$ $cm^3/(cm^2 \cdot s \cdot cm\ Hg)$, greater than about $5\times10^{-3}$ $cm^3/(cm^2 \cdot s \cdot cm\ Hg)$, or greater than about $5\times10^{-2}$ $cm^3/(cm^2 \cdot s \cdot cm\ Hg)$. In preferred embodiments, the oxygen permeance of the layer is less than about 0.5 $cm^3/(cm^2 \cdot s \cdot cm\ Hg)$.

In certain embodiments, the oxygen permeability coefficient of the layer is greater than about $5\times10^{-4}$ Barrer. In preferred embodiments, the oxygen permeability coefficient of the layer is greater than about $5\times10^{-2}$ Barrer, greater than about 5 Barrer, or greater than about 50 Barrer. In further preferred embodiments, the oxygen permeability coefficient of the layer is greater than about 500 Barrer. In other preferred embodiments, the oxygen permeability coefficient of the layer is greater than about 5,000 Barrer. In preferred embodiments, the oxygen permeability coefficient of the layer is less than about 20,000 Barrer.

In certain embodiments, the water vapor transmission rate of the layer is greater than about $1\times10^{-9}$ $cm^3/(cm^2 \cdot s)$ and less than about $1.5\times10^{-1}$ $cm^3/(cm^2 \cdot s)$. In preferred embodiments, the water vapor transmission rate of the layer is greater than about $1\times10^{-8}$ $cm^3/(cm^2 \cdot s)$. In further preferred embodiments, the water vapor transmission rate of the layer is greater than about $1\times10^{-7}$ $cm^3/(cm^2 \cdot s)$. In other preferred embodiments, the water vapor transmission rate of the layer is greater than about $1\times10^{-6}$ $cm^3/(cm^2 \cdot s)$, greater than about $1\times10^{-5}$ $cm^3/(cm^2 \cdot s)$, or greater than about $1\times10^{-4}$ $cm^3/(cm^2 \cdot s)$. In preferred embodiments, the water vapor transmission rate of the layer is less than about $1.5\times10^{-2}$ $cm^3/(cm^2 \cdot s)$.

In certain embodiments, the water vapor permeance of the layer is greater than about $1\times10^{-11}$ $cm^3/(cm^2 \cdot s \cdot cm\ Hg)$ and less than about $2\times10^{-3}$ $cm^3/(cm^2 \cdot s \cdot cm\ Hg)$. In preferred embodiments, the water vapor permeance of the layer is greater than about $1\times10^{-10}$ $cm^3/(cm^2 \cdot s \cdot cm\ Hg)$, or greater than about $1\times10^{-9}$ $cm^3/(cm^2 \cdot s \cdot cm\ Hg)$. In further preferred embodiments, the water vapor permeance of the layer is greater than about $1\times10^{-8}$ $cm^3/(cm^2 \cdot s \cdot cm\ Hg)$. In other preferred embodiments, the water vapor permeance of the layer is greater than about $1\times10^{-7}$ $cm^3/(cm^2 \cdot s \cdot cm\ Hg)$, or greater than $1\times10^{-6}$ $cm^3/(cm^2 \cdot s \cdot cm\ Hg)$. In preferred embodiments, the water vapor permeance of the layer is less than about $2\times10^{-2}$ $cm^3/(cm^2 \cdot s \cdot cm\ Hg)$.

In certain embodiments, the water vapor permeability coefficient of the layer is greater than about $1\times10^{-3}$ Barrer and less than about $1\times10^6$ Barrer. In preferred embodiments, the water vapor permeability coefficient of the layer is greater than about 0.01 Barrer, greater than about 0.1 Barrer, greater than about 1 Barrer, greater than about 10 Barrer, greater than about 100 Barrer, or greater than about $1\times10^3$ Barrer. In further preferred embodiments, the water vapor permeability coefficient of the layer is greater than about $1\times10^4$ Barrer and less than about $1\times10^5$ Barrer.

Another aspect provided herein is directed to a composition that forms a layer over skin such that the transepidermal water loss of the area treated with the composition is reduced or comparable to untreated skin. TEWL measurements can be made at any time on or after about 30 minutes time point, for example, at about 1-hour, about 4-hour, about 6-hour, about 12-hour, about 24-hour, about 30-hour, about 36-hour, about 48-hour, or between 48 hours and one week time point. In certain embodiments, the transepidermal water loss after application of the composition is less than about 40 $g/(m^2 \cdot hr)$. In preferred embodiments, the transepidermal water loss after application of the composition is less than about 20 $g/(m^2 \cdot hr)$. In further preferred embodiments, the transepidermal water loss after application of the composition is less than about 10 $g/(m^2 \cdot hr)$. In other preferred embodiments, the transepidermal water loss after application of the composition is less than about 5 $g/(m^2 \cdot hr)$, or less than about 1 $g/(m^2 \cdot hr)$.

Another aspect provided herein is directed to a composition that forms a layer over skin such that the skin hydration of the area treated with the composition is improved or comparable to untreated skin. Skin hydration measurements can be made at any time on or after about 30-minute time point, such as at about 1-hour, about 4-hour, about 6-hour, about 12-hour, about 24-hour, about 30-hour, about 36-hour, about 48-hour, or between 48 hours and one week time point. Skin hydration can be measured, for example, using a Corneometer pursuant to the procedure as described in H. Dobrev, "Use of Cutometer to assess epidermal hydration," *Skin Research and Technology* 2000, 6(4):239-244. In certain embodiments, the skin hydration after application of the composition is greater than about 20 arbitrary units (normalized hydration value) of Corneometer. In preferred embodiments, the skin hydration after application of the composition is greater than about 40 arbitrary units of Corneometer. In other preferred embodiments, the skin hydration after application of the composition is greater than about 60 arbitrary units of Corneometer, or greater than about 80 arbitrary units of Corneometer.

Skin hydration can also be measured, for example, using the procedure as described in Clarys et al., Hydration measurements of the stratum corneum: comparison between the capacitance method (digital version of the Corneometer CM 825®) and the impedance method (Skicon-200EX®), *Skin Research and Technology* 2011, 18(3):316-23. In certain embodiments, the skin hydration after application of the composition is greater than about 20 microSiemens. In preferred embodiments, the skin hydration after application of the composition is greater than about 50 microSiemens. In other preferred embodiments, the skin hydration after application of the composition is greater than about 100 microSiemens, or greater than about 200 microSiemens, or about 400 microSiemens.

Another aspect provided herein is directed to a composition that forms a layer on the skin that tightens the skin. The tightening effect which is caused by increasing the skin tension is quantified from a specimen formed from the composition in vitro by using the with the in-vitro curl test as described herein. In certain embodiments, the tension is increased by greater than 0.1 N/m. In preferred embodiments, the tension is increased by greater than 0.2 N/m. In preferred embodiments, the tension is increased by greater than 0.5 N/m, by greater than 1.0 N/m, by greater than 2.0 N/m, by greater than 5.0 N/m, by greater than 10 N/m, by greater than 20 N/m, by greater than 50 N/m, by greater than 100 N/m, by greater than 500 N/m, or by greater than 1,000 N/m.

Another aspect provided herein is directed to a composition that forms a layer on the skin such that the surface contour of the skin can be modulated. The "surface contour of the skin" is observed with Canfield 3-D Imaging System or visually with the comparative photos before and after the application of the test composition.

In preferred embodiments, the composition forms a layer that is cosmetically elegant and has the appearance of normal, healthy, and youthful skin of the subject to which the composition or layer is applied. Consequently, the layer may convey cosmetic and therapeutic benefits that reduce the appearance of any signs of ageing which include under eye bags, laugh lines, crow feets, forehead lines and wrinkles.

Another aspect provided herein is directed to a composition that forms a layer on the skin such that retraction time of the area treated with the composition is decreased comparing with untreated skin. Skin retraction time measurements can be made at any time on or after about 30 minutes time point, such as at about 1-hour, about 4-hour, about 6-hour, about 12-hour, about 24-hour, about 30-hour, about 36-hour, about 48-hour, or between 48 hours and one week time point. In certain embodiments, the skin retraction time after application of the composition is decreased by about 5% to about 75%. In preferred embodiments, the skin retraction time after application of the composition is decreased by greater than about 10%. In other preferred embodiments, the skin retraction time after application of the composition is decreased by greater than about 25%, or greater than about 50%.

In certain embodiments, provided herein are compositions, devices and methods for modifying skin function by formation of a layer over the skin of a subject that forms quickly and that is thin, durable, non-invasive, easy to use, and with skin-like properties.

Disclosed herein are compositions that can form a covering, layer, film, device, and/or prosthetic skin over the skin that have low tackiness and form quickly, resulting in a wearable, comfortable (maintains temperature and humidity similar to normal, healthy skin), breathable, thin, optically invisible, cosmetically elegant, flexible, stretchable, elastic and body-movement conforming, yet long-lasting covering, layer, film, device, and/or prosthetic skin, that can be comfortably worn to provide skin hydration and other therapeutic, aesthetic, and/or cosmetic benefits.

Provided here are novel compositions that are longer lasting and perform better than prior compositions, particularly during more demanding activities, for example, exercising, showering and swimming (in sea-water, fresh water or chlorinated water), steam room (heat at high humidity), and sauna (heat at low humidity). An additional benefit is that the extended wearability and/or durability of the layer does not require repeated applications to sustain its benefits. The layer formed can be worn over a period of about 24 hours or more without the need to reapply.

In particular, the layer formed from the compositions disclosed herein regulates transdermal transport properties of skin, helps maintain skin hydration by providing an additional barrier over skin against water vapor loss from the body into the environment, helps protect the body against external and internal assaults, such as environmental factors (e.g., heat, cold, wind, water, humidity), bodily fluids (e.g., blood, pus/liquor puris, urine, saliva, sputum, tears, semen, milk, or vaginal secretion), sebum, saline, seawater, soapy water, detergent water, chlorinated water, pathogens, allergens, and pruritogens, and helps maintain conditions conducive to skin repair during new skin layer formation such as wound-healing that minimize scar formation.

In addition to providing increased compliance with a once-daily, or less frequent, application of aesthetically pleasing compositions, users of such compositions benefit from the therapeutic effects. The compositions and methods described herein provide a more attractive alternative to current treatment options for conditions of compromised skin barrier function.

The present compositions are suitable for easy topical application to form an aesthetically invisible, elastic, skin-conforming covering, layer, film, device, and/or prosthetic skin, which can be safely worn on the skin. Materials used in the present compositions are preferably selected from the US Food and Drug Administration's list of Generally Regarded as Safe (GRAS) substances or equivalents thereof, or are otherwise safe for skin and/or body applications.

One aspect provided herein is directed to compositions that form a layer on a surface such as leather, glass, plastic, metal, ceramic, semiconductor, insulator, conductor, or the skin or the mucous membrane or the lip or the hair or the nail in-situ, i.e., in the location where the compositions disclosed herein are applied. The layer is preferably formed without the need of heating or UV or light or electrical or magnetic or pressure or sound exposure. The layer can be additionally formed with exposure to one or more of heating, UV, light, electricity, magnetism, pressure and sound. Another aspect provided herein is directed to compositions that form a layer on a surface such as leather, glass, plastic, ceramic, semiconductor, insulator, conductor, or metal, which is then applied over the skin or the mucous membrane or the lip or the hair or the nail of a subject.

In preferred embodiments, the composition further comprises one or more optics modifiers. In other preferred embodiments, the first part and/or the second part further independently comprise one or more optics modifiers or particles. Optics modifiers or particles introduce surfaces responsive to optical or photonic interaction, e.g., roughness for light scattering, thereby imparting desirable shine, glossy, glow, matte appearance beyond or comparable to that of normal, healthy skin, preferably avoiding a significantly more shiny and/or glossy appearance than normal skin. Suitable optics modifiers or particles include, for example, pigments, dyes, polymers such as nylon (e.g., nylon-6, nylon-10, nylon-12), silicone, acrylic, acrylates/carbamate or other polymer or copolymer beads or particles, polyethylene beads, polymethylmethacrylate beads, polystyrene beads, polyurethane beads; inorganics such as silica (e.g., silica and DMPA/isophthalic acid/SMDI copolymer, available as ChronoSphere® Opticals from Lonza Group), boron nitride, talc, mica, alumina, titania; metal such as silver nanoparticles; and silicone, acrylic, acrylates/carbamate or other polymer or copolymer beads or particles. In certain embodiments, the optics modifiers or particles have an average particle diameter of between about 1 μm and about 20 μm. In a preferred embodiment, the optics modifiers or particles have an average particle diameter of between about 0.1 μm and about 20 μm. In preferred embodiments, the optics modifiers or particles have an average particle diameter of 2 μm to 15 μm, and further preferably 5 to 10 μm.

Another aspect provided herein is directed to a composition that forms a layer that does not significantly change the shine and/or gloss of the area over which the composition is applied. Shine and/or gloss can be measured on a specimen formed from the composition in vitro, for example, using a Glossmeter pursuant to the ASTM D523 Specular Gloss test, at 20°, 60°, and/or 85° measurement angels. The light and measurement angel can be selected based on the anticipated gloss range. For example, if the measurement made at 60° is greater than about 70 gloss units (GU), the measurement angle should be changed to 20° to optimize measurement accuracy. Conversely, if the measurement made at 60° is less than about 10 GU, the measurement angle should be changed to 85° to optimize measurement accuracy. 45° or 75° measurement angle may also be used depending on the gloss of the substrate used for the test. Various materials can be used as substrate to mimic normal, healthy skin for the test, for example, Cowhide Tooling leather in natural color. Shine and/or gloss change is indicated by the percentage increase or decrease of gloss units in a measurement area after the treatment comparing to before treatment. In certain embodiments, the shine and/or gloss change of the area treated with the composition is less than about 20%. In preferred embodiments, the shine and/or gloss change of the area treated with the composition is less than about 10%. In further preferred embodiments, the shine and/or gloss change of the area treated with the composition is less than about 5%.

Another aspect provided herein is directed to a composition that forms a layer that is clear, transparent, and/or optically invisible. Another aspect provided herein is directed to a composition that forms a layer so that the area with the composition applied has minimal color change before and after the application, such as color L* scale change, color a* scale change, and/or color b* scale change. Color L* scale, color a* scale and color b* scale are the three L*a*b* color space specified by the International Commission on Illumination. Color L* scale, color a* scale and color b* scale changes can be measured on a specimen formed from the composition in vitro, for example, using a Minolta Color Meter pursuant to the ASTM E313 Calculating Yellowness and Whiteness Indices from Instrumentally Measured Color Coordinates. Various materials can be used as substrate to mimic normal, healthy skin for the test, for example, Cowhide Tooling leather in natural color.

In certain embodiments, the color L* scale change of the area treated with the composition is less than about 2. In preferred embodiments, the color L* scale change of the area treated with the composition is less than about 1.5. In other preferred embodiments, the color L* scale change of the area treated with the composition is less than about 1, or less than about 0.5. In certain embodiments, the color a* scale change of the area treated with the composition is less than about 2. In preferred embodiments, the color a* scale change of the area treated with the composition is less than about 1.5. In other preferred embodiments, the color a* scale change of the area treated with the composition is less than about 1, or less than about 0.5. In certain embodiments, the color b* scale change of the area treated with the composition is less than about 2. In preferred embodiments, the color b* scale change of the area treated with the composition is less than about 1.5. In other preferred embodiments, the color b* scale change of the area treated with the composition is less than about 1, or less than about 0.5.

Another aspect provided herein is directed to a composition that forms a layer that is translucent or opaque. In certain embodiments, the composition further comprises one or more colorants, including, but not limited to, pigments, dyes (including fluorescent dyes), FD&C colors, D&C colors, lake colors, other color-imparting compounds, and a combination thereof. Other suitable colorants are disclosed, for example, in the CTFA Cosmetic Ingredient Handbook, 2nd ed. 1992. In preferred embodiments, the color of the layer substantially matches the color of normal, healthy skin of the subject. In other preferred embodiments, the layer further comprises various colorants, pearlescents, patterns, designs, or a combination thereof, thus conveying make up, cosmetic, aesthetic, and/or decorative benefits.

In certain embodiments, a finishing composition may be applied with or over the layer during or after its formation to provide a desired tactile sensation or aesthetic look. For example, the finishing composition may provide a silky, soft and/or smooth tactile sensation or a dewy, fresh, matte, shiny or luminescent aesthetic look. In certain embodiments, the finishing composition comprises one or more of oils, esters or ethers, feel modifiers, tack modifiers, spreadability enhancers, adhesion modifiers, emulsifiers, emollients, surfactants, thickeners, film formers, humectants, preservatives, cosmetic agents, and/or therapeutic agents.

In certain embodiments, the finishing composition comprises optics modifiers or particles, colorants, pearlescents, patterns, and/or designs.

In certain embodiments, the finishing composition may be in various forms, for example, liquid, lotion, cream, ointment, serum, gel, spray, foam, mousse, spritz, powder, or other suitable forms.

Another aspect provided herein is directed to a composition that forms a layer that is clear, transparent, and/or optically invisible. Another aspect provided herein is directed to a composition that forms a layer so that the area with the composition applied has minimal color change before and after the application, such as color L* scale change, color a* scale change, and/or color b* scale change. Color L* scale, color a* scale and color b* scale are the three L*a*b* color space specified by the International Commission on Illumination. Color L* scale, color a* scale and color b* scale changes can be measured on a specimen formed from the composition in vitro, for example, using a Minolta Color Meter pursuant to the ASTM E313 Calculating Yellowness and Whiteness Indices from Instrumentally Measured Color Coordinates. Various materials can be used as substrate to mimic normal, healthy skin for the test, for example, Cowhide Tooling leather in natural color.

In certain embodiments, the color L* scale change of the area treated with the composition is less than about 2. In preferred embodiments, the color L* scale change of the area treated with the composition is less than about 1.5. In other preferred embodiments, the color L* scale change of the area treated with the composition is less than about 1, or less than about 0.5. In certain embodiments, the color a* scale change of the area treated with the composition is less than about 2. In preferred embodiments, the color a* scale change of the area treated with the composition is less than about 1.5. In other preferred embodiments, the color a* scale change of the area treated with the composition is less than about 1, or less than about 0.5. In certain embodiments, the color b* scale change of the area treated with the composition is less than about 2. In preferred embodiments, the color b* scale change of the area treated with the composition is less than about 1.5. In other preferred embodiments, the color b* scale change of the area treated with the composition is less than about 1, or less than about 0.5.

Another aspect provided herein is directed to a composition that forms a layer that is translucent or opaque. In certain embodiments, the composition further comprises one or more colorants, including, but not limited to, pigments, dyes (including fluorescent dyes), FD&C colors, D&C colors, lake colors, other color-imparting compounds, and a combination thereof. Other suitable colorants are disclosed, for example, in the CTFA Cosmetic Ingredient Handbook, 2nd ed. 1992. In preferred embodiments, the color of the layer substantially matches the color of normal, healthy skin of the subject. In other preferred embodiments, the layer further comprises various colorants, pearlescents, patterns, designs, or a combination thereof, thus conveying make up, cosmetic, aesthetic, and/or decorative benefits.

In certain embodiments, a finishing composition may be applied with or over the layer during or after its formation to provide a desired tactile sensation or aesthetic look. For example, the finishing composition may provide a silky, soft and/or smooth tactile sensation or a dewy, fresh, matte, shiny or luminescent aesthetic look. In certain embodiments, the finishing composition comprises one or more of oils, esters or ethers, feel modifiers, tack modifiers, spreadability enhancers, adhesion modifiers, emulsifiers, emollients, surfactants, thickeners, film formers, humectants, preservatives, cosmetic agents, and/or therapeutic agents.

In certain embodiments, the finishing composition comprises optics modifiers or particles, colorants, pearlescents, patterns, and/or designs.

In certain embodiments, the finishing composition may be in various forms, for example, liquid, lotion, cream, ointment, serum, gel, spray, foam, mousse, spritz, powder, or other suitable forms.

In certain embodiments wherein the composition is a two-part composition, the first part and the second part are applied either one at a time or in combination to form the layer.

In certain embodiments, the first part is anhydrous. Alternatively, the first part is an emulsion. In certain embodiments, the first part can be spread, sprayed or spritzed over skin.

In certain embodiments, the second part is anhydrous. Alternatively, the second part is an emulsion. In certain embodiments, the second part can be spread, sprayed or spritzed over skin.

Another aspect provided herein is directed to a composition that forms a layer on the skin, wherein the composition has a glass transition temperature about or below body temperature.

Another aspect provided herein is directed to a composition that forms a layer that has low tackiness and forms quickly. When the layer is "set-to-touch," it becomes substantially resistant to environmental factors, thus allowing the user to resume intended activities. When the layer is "tack-free," it becomes substantially resistant to surface friction and abrasion from environmental factors, thus allowing the user to further resume intended activities. Consequently, an appropriate set-to-touch time and tack-free time for the layer is important: a longer set-to-touch time and tack-free time would require the user to wait a longer time before resuming activities, affecting consumer compliance; while a shorter set-to-touch time and tack-free time would require faster handling, application and/or spreading of the composition, which is not attainable by all users, or may otherwise negatively affect the continuity, evenness, uniformity, and/or physical properties of the layer.

In preferred embodiments, the composition further comprises one or more optics modifiers. In other preferred embodiments, the first part and/or the second part further independently comprise one or more optics modifiers or particles. Optics modifiers or particles introduce surfaces responsive to optical or photonic interaction, e.g., roughness for light scattering, thereby imparting desirable shine, glossy, glow, matte appearance beyond or comparable to that of normal, healthy skin, preferably avoiding a significantly more shiny and/or glossy appearance than normal skin. Suitable optics modifiers or particles include, for example, pigments, dyes, polymers such as nylon (e.g., nylon-6, nylon-10, nylon-12), silicone, acrylic, acrylates/carbamate or other polymer or copolymer beads or particles, polyethylene beads, polymethymethacrylate beads, polystyrene beads, polyurethane beads; inorganics such as silica (e.g., silica and DMPA/isophthalic acid/SMDI copolymer, available as ChronoSphere® Opticals from Lonza Group), boron nitride, talc, mica, alumina, titania; metal such as silver nanoparticles; and silicone, acrylic, acrylates/carbamate or other polymer or copolymer beads or particles. In certain embodiments, the optics modifiers or particles have an average particle diameter of between about 1 μm and about 20 μm. In a preferred embodiment, the optics modifiers or particles have an average particle diameter of between about 0.1 μm and about 20 μm. In preferred embodiments, the optics modifiers or particles have an average particle diameter of 2 μm to 15 μm, and further preferably 5 to 10 μm.

In certain embodiments, the composition further comprises between 0.05% and 30% by weight one or more polymers and/or non-polymers that affects the set-to-touch time of the composition. Other suitable polymers include, but are not limited to, polytetrafluoroethylene (PTFE), poly (methyl methacrylate) (PMMA), polyethylene (PE or polyethene), polypropylene (PP or polypropene), polyvinylidene fluoride (PVDF), polyurethane, acrylate, polyester such as nylons, polyether, polycarbonate, polysulfone, polyphosphate, or a combination thereof. Suitable non-polymers include, but are not limited to, particles such as carbon, silica, boron nitride, metal oxides (e.g., zinc oxide, titanium dioxide) and salts such as carbonate salts (e.g., calcium, magnesium, sodium salts), sulfates, phosphates, borates, halogenated salts, or a combination thereof.

Set-to-touch time can be measured on test subjects, for example, using the Set-to-Touch Time and Tack-Free Time of Film Test described herein, as modified from ASTM D5895-03. Set-to-touch time can also be measured in vitro, for example, using the Set-to-Touch Time Film Test described herein, using suitable substrates, for example, polyurethane, polypropylene and/or Cowhide Tooling leather.

Tack-free time is measured on test subjects by using the Set-to-Touch Time and Tack-Free Time of Film Test described herein, as modified from ASTM D5895-03. Tack-free time can also be measured in vitro, by using the Set-to-Touch Time and Tack-Free Time of Film Test described herein over suitable substrates, for example, polyurethane, polypropylene, and Cowhide Tooling leather.

Another aspect provided herein is directed to a composition that forms a thin layer on the skin. Thickness of the layer affects both its breathability, invisibility, compressibility, and its skin occlusive effects. "Thickness" refers to the average thickness of the layer applied to a surface. Thickness of the layer formed can be measured in vitro, for example, on a cross-section of a layer using microscope having a stage or ocular micrometer. Thickness of the layer is measured on a specimen formed from the composition in vitro by using the ASTM D3767 Rubber-Measurement of Dimensions using the Mitutoyo Thickness Gauge test, modified to be used on free-standing film or on a layer over a substrate such as polyurethane, polypropylene, and Cowhide Tooling leather at room temperature and about 50% relative humidity. Polyurethane and polypropylene have surface conditions that are preferably used for the thickness measurement due to their smooth surface with low aspect ratio, allowing the layer to be easily removed as a free-standing layer. Cowhide Tooling leather has the preferred water absorption and grain surface conditions needed for the thickness measurement. Cowhide Tooling leather is commonly vegetable tanned and absorbs water readily and dries out quickly because the fiber structure is less compact than that of chrome tanned leather. Cowhide Tooling leather is "full grain," meaning the hair has been removed and the original grain remains. Thickness of the layer can also be measured on a specimen formed from the composition in vitro, for example, using the ASTM D-6132 Nondestructive Measurement of Dry Film Thickness of Applied Organic Coatings using the PosiTector Ultrasonic Coating Thickness Gauges test, modified to use polyurethane as substrate at room temperature and about 50% relative humidity.

The thickness measurement of the substrate is made before and after applying the composition, from which the difference in thickness before and after applying the composition indicates the layer thickness.

Another aspect provided herein is directed to a composition that forms a durable layer on the skin. The durability of the layer on the skin can be determined, for example, using the Film Durability on Skin test described herein.

5.1.1 Bifunctional Organopolysiloxane Polymer for Use with the Compositions and Methods Provided Herein In certain embodiments, the bifunctional organopolysiloxane polymer for use with the compositions and methods provided herein is a linear siloxane polymer. In certain embodiments, the bifunctional organopolysiloxane polymer for use with the compositions and methods provided herein is a branched siloxane polymer.

In certain embodiments, the linear siloxane polymers are dual functional low- to moderate- to high-molecular weight linear siloxane polymers containing one hydride functionality terminus and one unsaturated functionality terminus. The hydride functionality and the unsaturated functionality are each attached to a different silicon atom on opposite ends of the linear siloxane polymer. These materials are liquids having viscosities in the range of about 5 to about 100,000 cSt and low polydispersities. These materials are liquids having viscosities in the range of about 3 to about 200,000 cSt and low polydispersities. These materials are liquids having viscosities in the range of about 2 to about 400,000 cSt and low polydispersities. These materials are liquids having viscosities in the range of about 1 to about 800,000 cSt and low polydispersities. These materials are liquids having viscosities in the range of about 1 to about 1600,000 cSt and low polydispersities. These materials are liquids having viscosities in the range of about 1 to about 3200,000 cSt and low polydispersities.

In certain embodiments, the term "low polydispersity" may be understood to refer to a polydispersity less than about 1.6, more preferably less than about 1.4, most preferably less than about 1.2. The degree of polymerization of the siloxanes is preferably greater than 6, more preferably 6 to about 1000, most preferably about 10 to about 200. It is essential that the dual functional materials have a ratio of substantially 1:1 of unsaturated group termini to hydride group termini within each polymer molecule. In certain embodiments, the term "substantially 1:1" means that the ratio is within about 5% of 1:1, more preferably within about 3% of 1:1. The ratio of unsaturated group termini to hydride group termini may be estimated based on a combination of 1H NMR, GPC, or step-growth polymerization data. The most effective method for achieving this 1:1 ratio is a method of "living" anionic ring-opening polymerization ("living" AROP), described below.

In certain embodiments, dual functional low- to moderate- to high-molecular weight linear siloxane polymers have the molecular weights from about 3200 daltons to about 160000 daltons. In certain embodiments, dual functional low- to moderate- to high-molecular weight linear siloxane polymers have the molecular weights from about 4700 daltons to about 235000 daltons. In certain embodiments, dual functional low- to moderate- to high-molecular weight linear siloxane polymers have the molecular weights from about 6180 daltons to about 309000 daltons. In certain embodiments, dual functional low- to moderate- to high-molecular weight linear siloxane polymers have the molecular weights from about 3200 daltons to about 32000 daltons. In certain embodiments, dual functional low- to moderate- to high-molecular weight linear siloxane polymers have the molecular weights from about 4700 daltons to about 47000 daltons. In certain embodiments, dual functional low- to moderate- to high-molecular weight linear siloxane polymers have the molecular weights from about 6180 daltons to about 61800 daltons.

The unsaturated functionality is not particularly limited, and may be, for example, a vinyl, styryl, allyl, methallyl, hexenyl, octenyl or alkynyl group. The preferred unsaturated functionality is a vinyl group. The siloxane backbone may be, for example, a dialkylsiloxane derived from a cyclotrisiloxane, such as dimethylsiloxane, ethylmethylsiloxane, diethylsiloxane, dimethylsilylethylsiloxane, trifluoropropylmethylsiloxane, or aromatic substituted siloxanes such as diphenylsiloxane or phenylmethylsiloxane. Other possibilities resulting in siloxane-hydrocarbon copolymers consistent with "living" AROP include 2,2,5,5-tetramethyl-2,5-disila-1-oxacyclopentane and related ring-strained systems.

In certain embodiments, a siloxane polymer has a dimethylsiloxane backbone, an unsaturated group and a hydride group, as shown in formula (IV):

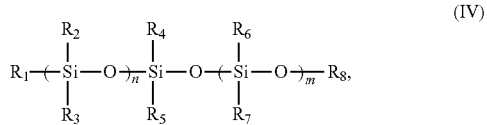

wherein one of $R_1$, $R_4$, $R_5$ and $R_8$ is an unsaturated group; one of $R_1$, $R_4$, $R_5$ and $R_8$ is a hydride group; the rest of $R_1$, $R_4$, $R_5$ and $R_8$ are $C_{1-20}$ alkyl groups; $R_2$, $R_3$, $R_6$ and $R_7$ are $C_{1-20}$ alkyl groups; and the sum of n and m is between 2 to 50.

A preferred siloxane polymer has a dimethylsiloxane backbone and a vinyl group as the unsaturated functionality, as shown in formula (V):

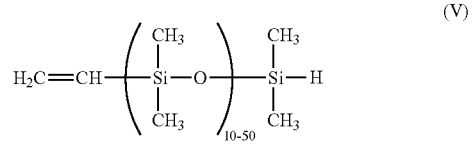

In certain embodiments, the monounsaturated-monohydride terminated siloxanes are stable, non-flammable liquids of moderate viscosity, which can be transferred by pouring, pumping, or by means of a syringe. In certain embodiments, the siloxanes may be compounded with a variety of reinforcing agents and thixotropic and non-thixotropic fillers, including fumed silica. In certain embodiments, monovinylphenyl-terminated siloxanes are advantageous due to the ability to control the optical properties (refractive index) and thermal properties.

In certain embodiments, the linear siloxane polymers can be prepared according to the methods described in the disclosure of U.S. Pat. No. 8,952,118, the disclosure of which is incorporated herein by reference in its entirety. The linear siloxane polymers can be also prepared according to other methods apparent to those of skill in the art.

5.1.2 Reinforcing Constituents for Use with the Methods Provided Herein

In preferred embodiments, the composition further comprises one or more reinforcing component(s). In certain embodiments, the reinforcing component is selected from surface treated carbon, silver, gold, diamond, copper, mica, zinc sulfide, zinc oxide, titanium dioxide, aluminum oxide, clay (e.g., $Al_2O_3$, $SiO_2$), chalk, talc, calcite (e.g., $CaCO_3$), barium sulfate, zirconium dioxide, polymer beads and silica (e.g., silica aluminates, calcium silicates, or surface treated silica (e.g., fumed silica, hydrated silica, or anhydrous silica)), or a combination thereof. Such reinforcing components reinforce the physical properties of the layer as discussed herein. In preferred embodiments, the reinforcing component is surface treated silica, for example, silica treated with hexamethyldisilazane, polydimethylsiloxane, hexadecylsilane or methacrylsilane. In further preferred embodiments, the reinforcing component is fumed silica, including fumed silica having been surface treated with hexamethyldisilazane.

In certain embodiments, the particles of the reinforcing component have an average surface area of between about 50 and about 1000 $m^2/g$. In preferred embodiments, the particles of the reinforcing component have an average surface area greater than about 300 $m^2/g$. In preferred embodiments, the particles of the reinforcing component have an average surface area of between about 600 and about 800 $m^2/g$. In preferred embodiments, the particles of the reinforcing component have an average surface area of between about 100 and about 600 $m^2/g$. In further preferred embodiments, the particles of the reinforcing component have an average surface area of between about 135 and about 250 $m^2/g$. In certain embodiments, the reinforcing component has an average particle diameter of between about 1 nm and about 20 μm. In preferred embodiments, the reinforcing component has an average particle diameter of between about 2 nm and about 1 μm, and further preferably between about 5 nm and about 50 nm.

In certain embodiments, the reinforcing component is suitable for cosmetic application on skin of a subject. In certain embodiments, the reinforcing component is suitable for therapeutic application on skin of a subject.

5.2 Additives for Use with the Compositions and Methods Provided Herein

In certain embodiments, the composition further comprises one or more additives. In certain embodiments, the first part and/or the second part further independently comprise(s) one or more additives. Suitable additives include, but are not limited to, feel modifiers, tack modifiers, spreadability enhancers, diluents, adhesion modifiers, volatile siloxanes, emulsifiers, emollients, surfactants, lubricants, thickeners, solvents, film formers, humectants, preservatives, pigments, skin permeation enhancers, optic modifiers, gas transport modifiers, liquid transport modifiers, pH modifiers, sensitizing modifiers, aesthetic modifiers, and a combination thereof. Additional suitable additives are disclosed in the International Nomenclature Cosmetic Ingredient (INCI) dictionary, which is incorporated herein by reference in its entirety. In preferred embodiments, the emulsifiers are alkoxydimethicone, alkyldimethicone, amodimethicone, sulfodimethicone, phosphodimethicone, borodimethicone, halodimethicone, fluorodimethicone, chlorodimethicone, bromodimethicone, charged dimethicone, and a combination thereof. In preferred embodiments, the emulsifiers are of linear-type, branch-type, elastomeric-type network, elastomeric-type organic/inorganic network, and a combination thereof.

In certain embodiments, the composition further comprises one or more additional agents. In certain embodiments, the first part and/or the second part further independently comprise(s) one or more additional agents, including cosmetic agents, therapeutic agents, stimuli-responsive agents, sensing agents, drug-delivery agents, optical agents, coloring agents, pigments, scattering agents, sorbing agents, temperature-active agents, heat-active agents, UV-active agents, light-active agents, sound-active agents, pressure-active agents, motion-active agents, radioactive agents, electrical agents, magnetic agents, and other beneficial agents.

5.2.1 Cosmetic Agents

Suitable cosmetic agents include, but are not limited to, moisturizers, sunscreens, UV protecting agents, skin-protectant agents, skin-soothing agents, skin-lightening agents, skin-brightening agents, skin-softening agents, skin-smoothening agents, skin-bleaching agents, skin-exfoliating agents, skin-tightening agents, cosmeceutical agents, vitamins, anti-oxidants, cell-signaling agents, cell-modulating agents, cell-interacting agents, skin tanning agents, anti-aging agents, anti-wrinkle agents, spot reducers, alpha-hydroxy acids, beta-hydroxy acids, ceramides, and a combination thereof.

5.2.2 Therapeutic Agents

Suitable therapeutic agents include, but are not limited to nerve modulating agents, pain-relievers, analgesics, anti-itching agents, anti-irritants, counterirritants, immunomodulating agents, immune system boosting agents, immune system suppressing agents, anthralin, fluocinonide, methotrexate, cyclosporine, pimecrolimus, tacrolimus, azathioprine, fluoruracil, ceramides, anti-acne agents (beta-hydroxy acids, salicylic acids, benzoyl peroxide), anti-flammatory agents, antihistamines, corticosteroids, NSAIDs (Non-Steroidal Anti-Inflammatory Drugs), blood-coagulating agents, antineoplastics, microbiome modulating agents, anti-septic agents, antibiotics, anti-bacteria agents, anti-fungal agents, anti-viral agents, anti-allergenic agents, skin protection agents, coal tars, insect-repelling agents, phototherapy agents, magnetotherapy agents, sonotherapy agents, thermotherapy agents, skin thermal regulating (cooling or heating) agents, or a combination thereof.

5.2.3 Beneficial Agents

Suitable beneficial agents include, but are not limited to, anti-oxidants, vitamins, vitamin D3 analogues, retinoids, minerals, mineral oil, petroleum jelly, fatty acids, plant extracts, polypeptides, antibodies, proteins, sugars, lipids, fatty acids, alcohols, esters, ceramides, chemokines, cytokines, hormones, neurotransmitters, lubricants, humectants, emollients, a combination thereof, and other similar agents beneficial for topical application known in the art.

5.3 Methods of Using

Another aspect provided herein is directed to a method for modifying skin functions, by including delivering agents (therapeutics and cosmetics). Non-limiting examples of skin functions that may be modified are skin barrier function; skin pigmentation; skin appearance, including but not limited to wards, acne (sebacic gland), melasma, ventiligo, psoriasis; contact dermatitis or other dermatitis such as stasis dermatitis; and pruritus. Non-limiting examples of therapeutics that may be included are anti-inflammatories, anticoagulants, antibiotics and antiseptics. Therapeutics and cosmetics are administered to a subject in need thereof, by applying to the subject's skin or body a composition as described herein.

Another aspect provided herein is directed to a method for treating conditions of compromised skin barrier function, including dermatological disorders, skin conditions, and wounds, in a subject in need thereof, by applying to the subject's skin or body a composition as described herein.

Another aspect provided herein is directed to a method for treating symptoms of conditions of compromised skin barrier function in a subject in need thereof, comprising applying to the subject's skin or body a composition as described herein, thereby treating one or more symptoms of a condition of compromised skin barrier function.

Another aspect provided herein is directed to a method for occluding skin of a subject in need thereof, comprising applying to the subject's skin or body a composition as described herein, thereby occluding the skin. "Occluding skin" means forming a barrier semi-permeable or impermeable to water vapor directly or indirectly over skin. In certain embodiments, the layer is semi-occlusive in that the composition forms a layer that is semi-permeable to water vapor. Alternatively, the layer is fully-occlusive in that the composition forms a layer that is impermeable to water vapor.

In another aspect provided herein, the occlusion enhances the efficacy of a topical drug also administered to the patient's skin. In one embodiment, the topical drug is a corticosteroid and the disease for the treatment of which the corticosteroid is administered is eczema. In one embodiment, occlusion restores the skin's barrier function. In one embodiment, occlusion enhanced drug delivery.

Occlusive Therapy with semi-occlusive or fully-occlusive layer has been well-established, particularly for atopic dermatitis treatment (for detailed reference: Misha M Heller, Eric S. Lee, Faranak Kamangar, Wilson Liao and John Y. M Koo (2012): Occlusive Therapy in Atopic Dermatitis, Atopic Dermatitis—Disease Etiology and Clinical Management, Dr. Jorge Esparza-Gordillo (Ed.), ISBN: 978-953-51-0110-9).

In certain embodiments, a film generated using the methods/compositions provided herein can impart the benefit of occlusion to modify and/or restore the barrier function of skin.

Another aspect provided herein is directed to a method for treating a subject for a condition of compromised skin barrier function, or to treat a symptom of such a condition, comprising applying to the subject's skin or body a composition as described herein.

Another aspect provided herein is directed to a method for delivering an agent to a subject to treat a condition of compromised skin barrier function, or to treat a symptom of such a condition, comprising applying to the subject's skin or body a composition as described herein, thereby delivering the agent to the subject.

Another aspect provided herein is directed to a method for delivering to a subject a therapeutic agent to treat a condition of compromised skin barrier function, or to treat a symptom of such a condition, comprising applying to the subject's skin or body a composition as described herein.

Another aspect provided herein is directed to a method to mask, conceal, or cover conditions of compromised skin barrier function, symptoms of compromised skin barrier function, and/or skin imperfections, comprising applying to the subject's skin or body a composition as described herein, thereby masking, concealing, or covering the area with the conditions of compromised skin barrier function, symptoms of compromised skin barrier function, and/or skin imperfections.

Another aspect provided herein is directed to a method for treating conditions of compromised skin barrier function, symptoms of compromised skin barrier function, and/or skin imperfections in conjunction with other treatment agent(s) (topical medication, cosmetics and/or personal care products, in the form of ointment, cream, lotion, gel, spray, foam, mousse, or other suitable forms), wherein said other treatment agent(s) is applied to the skin are first, then the composition disclosed herein is applied over such other treatment agent(s) to provide a durable barrier for the other treatment agent(s).

In certain embodiments, the condition of compromised skin barrier function is a dermatological disorder selected from eczema, psoriasis, ichthyosis, rosacea, chronic dry skin, cutaneous lupus, lichen simplex chronicus, xeroderma, acne, disease-driven secondary dermatological disorder, ulcer, and a combination thereof. In preferred embodiments, the condition of compromised skin barrier function is selected from eczema, psoriasis, ichthyosis, rosacea, and chronic dry skin.

Identification and/or pre-treatment of the area of skin function (e.g., washing, shaving, or otherwise preparing the area for treatment) may be performed. After the optional pre-treatment, the composition is applied to the area in need of treatment to form the layer over the entire or a portion of the area in need of treatment, thereby treating the conditions of skin function.

Another aspect provided herein is directed to a method of modifying the surface of the skin. In some embodiments, the surface of the skin is modified chemically by altering its surface pH. In some embodiments, the skin is modified by covering portions of its surface with melanin for UV protection. In some embodiments, the skin is modified by covering portions of its surface with silicone to reduce its friction. In some embodiments, the skin is modified physically, such that eye-bags and/or laugh-lines are reduced. In some embodiments, skin is modified by covering portions of its surface with pigments for cosmetic purposes. In some embodiments, skin is modified by covering portions of its surface with soft-focus elements to modify the appearance of the skin. In some embodiments, skin is modified by covering portions of its surface with components that allow for electrical responses, for example by incorporating graphene or magnetic particles, preferably in the first part.

Another aspect provided herein is directed to a method of modifying skin tension. A change in skin tension may modify the skin's surface contour and/or the skin's recoil dynamic after stress response. As individuals age, they generally lose skin tension and the recoil dynamic response of the skin.

The amount of the composition applied is determined by the size and location of the area to be treated as well as the type of conditions of skin function, e.g., compromised skin barrier function, to be treated.

The layer may remain over the area until the conditions of compromised skin barrier function resolve, or improve, or maybe removed after an appropriate period of time as determined by a skilled practitioner (e.g., a medical practitioner such as a physician) or by the subject. The application can be repeated as many times as needed in order to achieve a desired result.

In certain embodiments, provided herein is a method for delivering an agent to a subject, comprising in no particular order a) applying to said subject's skin the composition disclosed here; and b) applying to said subject's skin a metal catalyst; wherein said metal catalyst catalyzes an in situ polymerization of the bifunctional organopolysiloxane polymer, such that a film is formed on the skin, thereby delivering the agent to the subject; wherein the one or more agents is present in at least a) or b). In certain embodiments, step (a) occurs before step (b). In certain embodiments, step (a) occurs after step (b). In certain embodiments, step (a) and step (b) occur concurrently. In certain embodiments, the content of the first container and the content of the second container are pre-mixed and applied together.

In certain embodiments, provided herein is a method for forming a film on the skin of a subject, comprising in no particular order a) applying to said subject's skin the composition disclosed here; and b) applying to said subject's skin a metal catalyst; wherein said metal catalyst catalyzes an in situ polymerization of the bifunctional organopolysiloxane polymer, such that a film is formed on the skin, thereby delivering the agent to the subject; wherein the one or more agents is present in at least a) or b). In certain embodiments, step (a) occurs before step (b). In certain embodiments, step (a) occurs after step (b). In certain embodiments, step (a) and step (b) occur concurrently. In certain embodiments, the content of the first container and the content of the second container are pre-mixed and applied together.

In some embodiments, the catalyst catalyzes the composition provided herein an in situ polymerization of the composition such that a film is formed on the skin.

In some embodiments, provided herein is a film removing cleanser for use in removing a film on skin of a subject. when the film removing cleanser is applied to a film, it breaks down the components of the film such that the film may be removed from the skin. In some embodiments, the film cleanser removes the film by wetting the film, penetrating the film, swelling the film and releasing the film from the skin.

In certain embodiments, the compositions and methods provided herein can be used to treat, prevent, or ameliorate the symptoms of skin conditions. The skin conditions include, but are not limited to, itchy skin, raw skin, dry skin, flaking or peeling skin, blisters on the skin, redness, swelling or inflammation of the skin, and oozing, scabbing or scaling skin. Skin conditions also include compromised skin barrier conditions caused by laser, light or chemical peel treatment.

In certain embodiments, the compositions and methods provided herein can be used to treat, prevent, or ameliorate the symptoms of wounds. The wounds include injuries to the skin wherein the skin is torn, cut or punctured. Wounds include open wounds, for example, abrasions, lacerations, incisions, punctures, avulsions, or amputations. Wounds also include burn wounds, a type of injury to skin and/or flesh caused by heat, electricity, wind, chemicals, light, radiation or friction.

In certain embodiments, the compositions and methods provided herein can be used to treat, prevent, or ameliorate the symptoms of dermatological disorders. The dermatological disorders include disorders that cause at least one symptom on the skin of a subject that may require medical treatment. Dermatological disorders may be caused by, among other things, autoimmune disorders and/or environmental factors, such as allergens or chemicals. Examples of symptoms of dermatological disorders include, but are not limited to, itchy skin, dry skin, crusting, blistering, or cracking skin, dermatitis, skin edema, or skin lesion formation. Dermatological disorders include, but are not limited to, eczema, psoriasis, ichthyosis, rosacea, chronic dry skin, cutaneous lupus, lichen simplex chronicus, xeroderma, acne, disease-driven secondary dermatological disorder, and ulcer.

In certain embodiments, the compositions and methods provided herein can be used to treat, prevent, or ameliorate the symptoms of eczema. The eczema includes, e.g., atopic eczema, atopic dermatitis, contact dermatitis, phototoxic dermatitis, xerotic eczema (also known as asteatotic eczema, eczema craquele or craquelatum, winter itch, or pruritus *hiemalis*), seborrheic dermatitis (or seborrhoeic eczema), dyshidrosis (also known as dyshidrotic eczema, pompholyx, vesicular palmoplantar dermatitis, or housewife's eczema), discoid eczema (also known as nummular eczema, exudative eczema, microbial eczema), venous eczema (also known as gravitational eczema, stasis dermatitis, varicose eczema), dermatitis herpetiformis (also known as Duhring's Disease), neurodermatitis (also known as lichen simplex chronicus, localized scratch dermatitis), autoeczematization, and retinoid-induced dermatitis.

In certain embodiments, the compositions and methods provided herein can be used to treat, prevent, or ameliorate the symptoms of psoriasis. The psoriasis includes, e.g., psoriasis vulgaris (also known as plaque psoriasis), psoriatic erythroderma, pustular psoriasis (including von Zumbusch, Palmoplantar and Acropustulosis psoriasis), drug-induced psoriasis, inverse psoriasis, seborrheic-like psoriasis and guttate psoriasis.

In certain embodiments, the compositions and methods provided herein can be used to treat, prevent, or ameliorate the symptoms of ichthyosis. The ichthyosis includes, e.g., ichthyosis vulgaris, acquired ichthyosis, X-linked ichthyosis, congenital ichthyosiform erythroderma, nonbullous (nbCIE), epidermolytic hyperkeratosis (bullous ichthyosis, bCIE), Harlequin type ichthyosis, ichthyosis bullosa of Siemens, ichthyosis hystrix, Curth-Macklin type, Hystrix-like ichthyosis with deafness, Lamellar ichthyosis, type 1, Lamellar ichthyosis, type 2, Lamellar ichthyosis, type 3, Lamellar ichthyosis, type 4, Lamellar ichthyosis, type 5, CHILD Syndrome, Conradi-Hünermann syndrome, ichthyosis follicularis with alopecia and photophobia syndrome, Keratitis-ichthyosis-deafness syndrome, Netherton syndrome, Neutral lipid storage disease with ichthyosis, adult Refsum disease, ichthyosis and male hypogonadism, Sjögren-Larsson syndrome, and photosensitive trichothiodystrophy (IBIDS syndrome).

In certain embodiments, the compositions and methods provided herein can be used to treat, prevent, or ameliorate the symptoms of rosacea. The rosacea includes, e.g., erythematotelangiectatic rosacea, papulopustular rosacea, phymatous rosacea (e.g., rhinophyma), and granulomatous rosacea.

In certain embodiments, the compositions and methods provided herein can be used to treat, prevent, or ameliorate the symptoms of cutaneous lupus. The cutaneous lupus includes, e.g., acute cutaneous lupus, subacute cutaneous lupus, chronic cutaneous lupus, chilblain lupus erythematosus, discoid lupus erythematosus, lupus erythematosus-lichen planus overlap syndrome, lupus erythematosus panniculitis, tumid lupus erythematosus and verrucous lupus erythematosus.

In certain embodiments, the compositions and methods provided herein can be used to treat, prevent, or ameliorate the symptoms of acne. The acne includes, e.g., acne vulgaris, acne aestivalis, acne conglobate, acne cosmetic, acne fulminans, acne keloidalis nuchae, acne mechanica, acne medicamentosa (also known as drug-induced acne, e.g., steroid acne), acne miliaris necrotica, acne necrotica, acne rosacea, and hidradenitis suppurativa.

In certain embodiments, the compositions and methods provided herein can be used to treat, prevent, or ameliorate the symptoms of disease-driven secondary dermatological disorder. The disease-driven secondary dermatological disorder refers to a dermatological condition that may require treatment and was caused by or is associated with a non-dermatological disorder. The non-dermatological disorder includes disorders not primarily associated with the skin but which may result in, be associated with, or have a secondary manifestation of a skin condition, for example, a disorder of the circulatory system or metabolism of the subject. Disease-driven secondary dermatological disorders include, for example, an ulcer caused by diabetes mellitus (e.g., diabetic foot ulcer), a bacterial, viral or fungal infection, cancer, pressure (e.g., a bedsore), blood disorders, conditions affecting the nervous system (e.g., neuropathic ulcers (also known as "mal perforans")), conditions affecting the nervous system (e.g., arterial insufficiency ulcers (also known as "ischemic ulcers") or vascular ulcers), and/or a chronic wound.

5.4 Kits for Use with the Compositions and Methods Provided Herein

Another aspect provided herein is directed to a kit for use in modifying skin condition of a subject; in treatment of conditions of compromised skin barrier function. In certain embodiments, the kit comprises (i) a composition disclosed herein, and (ii) instructions for use.

In certain embodiments, the kit comprises (i) a first part disclosed herein (as described in the fifth and following paragraphs of Section 5.1), (ii) a second part disclosed herein (as described in the fifth and following paragraphs of Section 5.1), and (iii) instructions for use. In preferred embodiments, the first part and the second part are prevented from coming into contact prior to use. In preferred embodiments, the first part and the second part are packaged in separate containers or compartments, and applied one at a time or mixed together prior to or upon use.

In certain embodiments, the kit further comprises a finishing composition. In certain embodiments, the kit further comprises a cleanser suitable for removing the layer from the skin, e.g., the cleansers disclosed in U.S. Pat. No. 8,691,202. In certain embodiments, the kit further comprises one or more sponge(s), cushion(s), brush(es), swab(s), and/or mirror(s).

Another aspect provided herein is directed to a device formed by application of any of the compositions disclosed herein. Another aspect provided herein is a prosthetic device, for example, a prosthetic skin, that modulates moisture retention, oxygen permeability and water vapor permeability on the skin formed by application of any of the composition disclosed herein. Another aspect provided herein is a prosthetic device, for example, a prosthetic skin, that modulates optical appearance on the skin formed by application of any of the composition disclosed herein. Another aspect provided herein is a prosthetic device, for example, a prosthetic skin, that modulates mechanical responses of the skin formed by application of any of the composition disclosed herein. Another aspect provided herein is a prosthetic device, for example, a prosthetic skin, that modulates electrical responses of the skin (for example by incorporating graphene or magnetic particles in the first part or in the second part of the composition disclosed herein at, e.g., in the fifth and following paragraphs of Section 5.1) formed by application of any of the composition disclosed herein. Another aspect provided herein is a prosthetic device, for example, a prosthetic skin, that modulates magnetic responses of the skin formed by application of any of the composition disclosed herein. Another aspect provided herein is a prosthetic device, for example, a prosthetic skin, that modulates pressure responses of the skin formed by application of any of the composition disclosed herein. Another aspect provided herein is a prosthetic device, for example, a prosthetic skin, that modulates pH responses of the skin formed by application of any of the composition disclosed herein. Another aspect provided herein is a prosthetic device, for example, a prosthetic skin, that modulates temperature responses of the skin formed by application of any of the composition disclosed herein. Another aspect provided herein is a prosthetic device, for example, a prosthetic skin, that modulates heat responses of the skin formed by application of any of the composition disclosed herein. Another aspect provided herein is a prosthetic device, for example, a prosthetic skin, that modulates sound responses of the skin formed by application of any of the composition disclosed herein.

In certain embodiments, provided herein is a kit for the formation of a film over the skin of a subject, wherein the kit comprises a) a first container comprising the composition disclosed here; and b) a second container comprising metal catalyst.

Physical properties of the compositions were measured using the methods (either standard or described herein) and devices set forth. Such methods and devices are merely exemplary, and other tests, methods, materials, and/or devices may be known or developed appropriate to test the properties of the compositions disclosed.

Unless otherwise specified, all properties of compositions, layers and/or devices disclosed herein are measured at room temperature (about 22-25° C.) and about 1 atmosphere air pressure.

5.5 Assays for Use with the Compositions and Methods Provided Herein

The following assays can be used to demonstrate the properties of the film generated with the composition and methods provided herein.

5.5.1 Rheometer Viscosity Measurement Test

The following test method may be used to determine the dynamic viscosity (Pa·s) of fluid materials at $0.5\ s^{-1}$, using a Bohlin CVO100 Rheometer (Malvern Instruments) mounted with 20 mm Parallel plate geometry. Similar Rheometers can be used for viscosity measurements. For each material tested, at least 3 samples are measured, and average viscosity and standard deviation of the measurements are recorded.

About 1 g of each test sample is required. Visually inspect the sample to ensure the sample appears uniform. Turn on the Bohlin Rheometer and the temperature controller; start the Bohlin software and load the viscosity stability test template; install the geometry and zero the instrument. Make sure that both the geometry and plate are clean, which is critical for accurate test results. Place about 1 g of the test sample onto the bottom plate of the Rheometer in a mound centered below the geometry. Lower the geometry to the correct gap (about 250 μm). Clean any excess sample from the sides of the geometry using the flat end of a spatula. Start the test and allow the test to run to completion, then record the viscosity (Pa·s) data.

In certain embodiments, a film generated with the compositions and methods provided herein has particular dynamic viscosity. In certain embodiments, the dynamic viscosity can be determined using the assay of the Rheometer Viscosity Measurement Test provided herein.

5.5.2 Film Durability on Skin Test

Application of Test Composition. Healthy subjects (at least 3) are selected irrespective of age, race or gender. Tests are conducted at room temperature and about 50% relative humidity. Drawn $4\times 4\ cm^2$ square outlines on selected volar forearm areas using a standard template as guide. Using a balance, weigh out appropriate amounts (e.g., about 0.1 g to about 0.3 g) of the test composition (or about 0.1 g of the first part and about 0.15 g of the second part in cases of a two-part composition) onto weigh boats (in cases of a two-part composition, do not mix). Apply the test composition evenly over the $4\times 4\ cm^2$ squares on the forearm using a fingertip, preferably wearing finger cot. Make sure that all areas of the squares are covered by the composition. In case of a two-part composition, a clean fingertip or fresh finger cot should be used to spread the second part gently over the first part, covering the entire first part area.

Measurement. The composition is allowed to sit untouched over the area for about 15 minutes. The subject is then allowed to resume daily activities. The subjects are permitted to conduct either only routine daily activities, or routine daily activities with demanding activities, for example, exercising, swimming, steam room, sauna, and the like. The type and length of each demanding activity are recorded. The layers formed by the test composition are left on skin for about 24 hours or more. At certain time points after application of the composition, durability of layers are assessed by measuring the percentage of the area intact on the skin using an 8×8 square grid of $0.5\times 0.5\ cm^2$ each (total 64 squares). Any excess layer outside of the $4\times 4\ cm^2$ square area is not considered in the evaluation. Each square is only considered to be durable if there is no visible imperfection, e.g., seams, flaking, cracking, and/or peeling, of the layer. Record the observations.

In certain embodiments, a film generated with the compositions and methods provided herein has particular film durability. In certain embodiments, the film durability can be determined using the assay of the Film Durability on Skin Test provided herein.

5.5.3 Set-to-Touch Time and Tack-Free Time of Film Test

This method was modified from ASTM D5895-03 Evaluating Drying or Curing During Film Formation of Organic Coatings Using Mechanical Recorders. The materials and application of test composition to the selected subjects are the same as described in the Film Durability on Skin Test. The test can also be conducted on other substrates instead of human skin, for example, on Cowhide Tooling leather in natural color, polyurethane, or polypropylene substrates with comparable results. For each composition tested, at least 3 samples are tested, and average set-to-touch time, average tack-free time and standard deviation of the measurements are recorded.

Measurement. Start a timer when the test composition (or the second part in case of a two-part composition) is applied to the entire test area on the forearm. Allow the composition to sit untouched over the area for a certain period of time, e.g., 30 seconds or one minute. At certain time points, touch one corner of the test area lightly using a fingertip, and visually evaluate: first the presence or absence of any test composition on the fingertip (Set-to-Touch Time); then the presence or absence of any film surface being pulled up by the fingertip (Tack-Free Time of Film Test). Repeat the fingertip evaluation on untouched portions of the test area at a certain time interval, e.g., every 15 seconds or 30 seconds or one minute. The time at which no more test composition is observed on the fingertip is reported as the "set-to-touch time" of the test composition. The time at which no more film surface is pulled up by the fingertip is reported as the "tack-free time" of the test composition.

In certain embodiments, a film generated with the compositions and methods provided herein has particular set-to-touch time and tack-free time. In certain embodiments, the set-to-touch time and tack-free time can be determined using the assay of the Set-to-Touch Time and Tack-Free Time of Film Test provided herein.

5.5.4 Set-to-Touch Time and Tack-Free Time of Film Test In-Vitro

This method was modified from ASTM D5895-03 Evaluating Drying or Curing During Film Formation of Organic Coatings Using Mechanical Recorders. The materials and application of test composition to the selected substrates are described as follows: Place a 50-micron spacer (for example, one layer of 3M Magic Scotch Tape) onto the substrate sheet size 4.5"×1.5", forming an opening rectangular of 3.75"×

0.75", exposing the substrate surface. Apply test composition onto the substrate, then gliding the glass slide back and forth along the spacer edges to deposit a smooth and uniform layer of test composition. The test can also be conducted on many substrates such as on Cowhide Tooling leather in natural color, polyurethane, or polypropylene substrates with comparable results. For each composition tested, at least 3 samples are tested, and average set-to-touch time, average tack-free time and standard deviation of the measurements are recorded.

Measurement. Start a timer when the test composition (or the second part in case of a two-part composition) is applied to the entire test area on the substrate. Allow the test composition to sit untouched over the area at room temperature and ambient humidity for a certain period of time, e.g., 30 seconds or one minute. At certain time points, place a 1.5 cm×4 cm polypropylene sheet on the surface of the test composition, then place a 15 g weight on top of polypropylene sheet. Wait for 2 seconds, before removing the weight and the polypropylene sheet from the surface of the test composition. Visually evaluate: first the presence or absence of any test composition on the polypropylene sheet. Repeat the polypropylene sheet evaluation on untouched portions of the test area at a certain time interval, e.g., every 15 seconds or 30 seconds or one minute. The time at which no more test composition on the polypropylene sheet is observed is reported as the "set-to-touch time" of the test composition. After "set-to-touch time" is reported, transfer the specimen to the 30-degree slope surface to evaluate the "tack-free time". Place the specimen 6 inches up along the slope surface away from the lowest point and secure the specimen on the slope surface. Drop a 1/32" diameter stainless steel ball onto the top part of the film surface from a distance an inch above the film surface. Observe the movement of the stainless steel ball on the film surface as the ball trying to roll down on its own gravity. Report "tack-free time" when the ball is able to roll from the top to the bottom part of the film surface continuously, without any interruption from the frictional film surface as the film becomes tack-free.

In certain embodiments, a film generated with the compositions and methods provided herein has particular set-to-touch time and tack-free time. In certain embodiments, the set-to-touch time and tack-free time can be determined using the assay of the Set-to-Touch Time and Tack-Free Time of Film Test in-vitro provided herein.

5.5.5 Peel Adhesion Test

This test method for adhesive force was developed in accordance with ASTM C794 Adhesion-in-Peel of Elastomeric Joint Sealants. Instron 3342 single column tension/compression testing system (Instron, Norwood, Mass.) with 100N load cell (Instron #2519-103) mounted with extension grip geometry may be used, with polypropylene sheet of 1/32" thickness as test substrate. Other similar equipment and other soft, flexible test substrates can also be used to measure the peeling force. The materials and application of test composition to the selected substrates are described as follows: Place a 50-micron spacer (for example, one layer of 3M Magic Scotch Tape) onto the substrate sheet size 4.5"× 1.5", forming an opening rectangular of 3.75"×0.75", exposing the substrate surface. Apply test composition onto the substrate, then gliding the glass slide back and forth along the spacer edges to deposit a smooth and uniform layer of test composition. Allow the test composition to sit untouched over the area at room temperature and ambient humidity for 3 hours. Then, place a silicone adhesive tape (Mepitac) of 0.75" width on top of the film to fully cover the film surface on the polypropylene substrate, ready for measurement. For each material tested, at least 3 samples are measured, and average peeling force and standard deviation of the measurements are recorded.

Measurement. Partially peel the silicone tape-covered test specimen at one end by hand to separate enough of the silicone tape-covered film from the polypropylene substrate for effective grip by extension grip geometry mounts of the instrument. Secure each peeling side in its own instrument grip. Make sure the strips are clamped substantially parallel to the geometry. Perform the extension test at a rate of 1 mm/s until the two peeling strips separate completely from each other. Record the peeling force vs. time data. The sample's average peeling force (N/m) is calculated by averaging the instantaneous force (N) measured by the instrument during the experiment normalized by the sample width (0.75" or 0.019 m).

In certain embodiments, a film generated with the compositions and methods provided herein has particular adhesive force. In certain embodiments, the adhesive force can be determined using the assay of the Peel Adhesion Test provided herein.

5.5.6 Curl Test for Surface Tension of Curved Specimen

The deposition of the test article on substrate such as skin or elastic band or parafilm results in residual compressive stress within the film due to volume loss (strain), which in turn translate to the tensile stress on the underneath substrate. The combined result of the film deposited on substrate could be observed and quantified based on the level of surface curvature of the substrate after the deposition of the film.

To prepare the test article for curl test, first the test article was deposited onto either an elastic synthetic rubber sheet or a parafilm substrate as described earlier in the application of test composition to the selected substrates. The materials and application of test composition to the selected substrates are described as follows: Place a 50-micron spacer (for example, one layer of 3M Magic Scotch Tape) onto the substrate sheet size 4.5"×1.5", forming an opening rectangular of 3.75"× 0.75", exposing the substrate surface. Apply test composition onto the substrate, then gliding the glass slide back and forth along the spacer edges to deposit a smooth and uniform layer of test composition. Allow the test composition to sit untouched over the area at room temperature and ambient humidity for 24 hours.

Measurement. Use a Vernier Caliper to measure the end-to-end distance of the width side of the test specimen that is curved upward. The end-to-end distance refers to the chord length, forming an incomplete upward circle where subsequent calculation of corresponding radius of the circle is computed. Report the radius value and its reciprocal as the "curvature" value. Use the curvature value to calculate the surface tension incurred on the substrate. In the case of originally curved surface with inherent surface tension such as skin, the change in surface tension incurred by the deposited top layer, will modify the inherent surface tension accordingly.

In certain embodiments, a film generated with the compositions and methods provided herein has particular surface tension. In certain embodiments, the surface tension can be determined using the assay of the Curl Test for Surface Tension of Curved Specimen provided herein.

5.5.7 Cyclic and Extension Pull Test

These test methods for Cyclic Tensile Residual Strain (Instant Residual Strain), Cyclic Tensile Hysteresis Loss Energy, Tensile (Young's) Modulus, Shear Modulus, Tensile Strength/Maximum Stress, Fracture Strain, and Fracture Toughness was developed to be better suited for the specimens disclosed herein in compliance with ASTM D638, ASTM D412, ASTM D1876 test guidelines. Instron 3342 single column tension/compression testing system (Instron, Norwood, Mass.) with 100N load cell (Instron #2519-103) mounted with extension grip geometry may be used. Other similar equipment can also be used to measure the properties tested herein. For each material tested, at least 3 samples are measured, and average results and standard deviation of the measurements are recorded.

About 10 g of the composition tested is needed for each sample. The samples are cast inside dumbbell shaped molds mounted on Teflon, consistent with the ASTM D638 guidelines. The dimensions of the "neck" of the mold are about 20 mm in length, about 5 mm in width and about 1.5 mm in depth. The dimensions of the "handles/bell" of the mold are about 20 mm in length, about 15 mm in width and about 1.5 mm in depth, which provides adequate area to insure secure slip-free grip during testing. Level the top surface of the filled mold with a smooth microscope slide. Ensure that the molds are filled without voids and the top surface is smooth. The casted samples are allowed to fully cure and dry for about 20 to about 30 hours. The specimens formed are extracted from their individual molds by means of a spatula. Width and thickness of the "neck" of the finished specimens are measured with a caliper, recorded and input into the instrument. The Area of the "neck" portion of the specimen is calculated by its width and thickness.

Layers formed by compositions disclosed herein can also be tested once separated from the substrates. Such a layer can be formed or trimmed into a rectangular shape, and the Area of a cross-section of a layer can be calculated by its width and thickness. In such as case, the ends of the rectangular specimen would be considered the "handle/bell" portions whereas the middle of the rectangular specimen would be considered the "neck" portion.

Mechanical characterization of specimens is carried out on the Instron 3342 (Instron, Norwood Mass.) equipped with 100N load-cell. Dumbbell or rectangular shaped specimens are mounted onto the instrument via Instron 2710-101 grips on each end, which are modified to insure the specimens do not slip or fail inside the grips during testing. The specimen is mounted onto the instrument such that all the rectangular "handle/bell" portions of the specimen and none of the "neck" of the specimen are fixed within the instrument grips. Make sure that the specimen is mounted substantially vertical in both vertical planes. The instrument grip distance is adjusted such that the sample is at neutral extension as indicated by the instrument force being close to zero (±0.01 N).

Two types of tests are performed sequentially on each specimen, first the Cyclic Test followed by the Extension Pull Test. It is noted that the Cyclic Test has negligible effects on the result of the Extension Pull Test on the same specimen. Each test is preprogrammed into the instrument.

Cyclic Test: The Cyclic Test is designed to determine the elasticity of the tested materials by measuring Cyclic Tensile Residual Strain (Instant Residual Strain). Generally, the more elastic the material, the faster it returns to its original shape after deformation. Lower Cyclic Tensile Residual Strain scores indicate better elasticity. For perfectly elastic materials, the Cyclic Tensile Residual Strain and cycle test area should approach zero.

The specimen is mounted onto the instrument as described above. Stretch the specimen slightly at about 1 mm/s by raising the geometry until a force of 0.06-0.08 N is registered by the instrument, record the stretched length of the "neck" portion of the specimen as the initial specimen length. Cyclic extension is performed at about 1 mm/s to a maximum extension of 15% of initial specimen length. A total of 15 (and up to 100) cycles are executed and the stress strain data is recorded.

The Cyclic Tensile Modulus is calculated as the straight line slope of the stress-strain curve of first cycle between 1% and 4% strain. The R squared value of the linear fit should be above 0.99 or the test data should be recorded as outlier and discarded. The Cyclic Tensile Residual Strain is calculated for each cycle as the strain difference between the loading and unloading curves at half the maximum stress achieved during the first cycle. The Cyclic Tensile Residual Strain for the first cycle as well as the average Cyclic Tensile Residual Strain for the 2nd through 12th cycles are recorded. The area bound by the loading and unloading curves of each cycle is also calculated as Cyclic Tensile Hysteresis Loss Energy. Good agreement is observed between the Cyclic Tensile Residual Strain and the calculated cycle area.

The majority of the specimens formed by the compositions disclosed herein are sufficiently flexible and elastic such that the Cyclic Test could be repeated on the same sample without a significant change in calculated properties, which suggests that this test did not result in long lasting changes to the tested specimens.

Extension Pull Test: The Extension Pull Test was used to determine the stiffness and stretchiness/flexibility of a material by measuring the Tensile/Young's Modulus and fracture strain, respectively.

The specimen is mounted onto the instrument as described above. Stretch the specimen slightly at about 10 mm/s by raising the geometry until a force of 0.01-0.02 N is registered by the instrument, record the stretched length of the "neck" portion of the specimen as "Original Length." The extension Tensile/Young's Modulus is calculated as the straight line slope of the stress-strain curve between 6% and 11% strain. The R squared value of the linear fit should be above 0.99 or the Tensile/Young's Modulus is calculated from a more linear 5% strain range on the stress strain curve.

The Shear Modulus is determined from the same strain range as the Tensile/Young's Modulus. Shear Modulus is calculated as the slope of the best line fit between recorded stress and $\alpha - 1/\alpha^2$, where a is 1 plus the instantaneous strain.

Stretch the specimen at about 10 mm/s until it is broken at one side or completely. Record the force applied at the time when the specimen is broken as the "Maximum Tensile Force." Record the length of the "neck" portion of the specimen when it is broken extended beyond the Original Length of the specimen as the "Maximum Elongation Length." Tensile Strength/Maximum Stress is calculated as the Maximum Tensile Force over the Area of the "neck" portion of the specimen. Fracture Strain is calculated as the Maximum Elongation Length as percentage of the Original Length.

Fracture Toughness ($kJ/m^3$) is calculated as the area under the stress-strain curve in the Extension Pull Test. The Yield Strain is determined as the strain at which the measured stress differed by more than 10% from the Neo-Hookean stress; the multiple of Shear Modulus and $(\alpha - 1/\alpha^2)$.

In certain embodiments, a film generated with the compositions and methods provided herein has particular Cyclic Tensile Residual Strain (Instant Residual Strain), Cyclic Tensile Hysteresis Loss Energy, Tensile (Young's) Modulus, Shear Modulus, Tensile Strength/Maximum Stress, Fracture Strain, and Fracture Toughness. In certain embodiments, the Cyclic Tensile Residual Strain (Instant Residual Strain), Cyclic Tensile Hysteresis Loss Energy, Tensile (Young's)

Modulus, Shear Modulus, Tensile Strength/Maximum Stress, Fracture Strain, and Fracture Toughness can be determined using the assay of the Cyclic and Extension Pull Test provided herein.

5.5.8 Transepidermal Water Loss (TEWL) Measurement Test

Evaporative water loss measurements provide an instrumental assessment of skin barrier function. Evaporimetry with TEWL Probe is fully described in Grove et al., Comparative metrology of the evaporimeter and the DermaLab® TEWL probe, *Skin Res. & Tech.* 1999, 5:1-8 and Grove et al., Computerized evaporimetry using the DermaLab® TEWL probe, *Skin Res. & Tech.* 1999, 5:9-13. The guidelines established for using the Servo Med Evaporimeter described by Pinnagoda (Pinnagoda et al., Guidelines for transepidermal water loss (TEWL) measurement, *Contact Dermatitis* 1990, 22:164-178) are appropriate for the DermaLab® TEWL Probe as well.

Evaporative water loss measurements can be made using a recently calibrated Servo Med Evaporimeter. Alternatively, these measurements can be made using a recently calibrated cyberDERM RG1 Evaporimeter System (Broomall, Pa.) with TEWL Probes (manufactured by Cortex Technology of Hadsund, Denmark and available in the US through cyberDERM, Inc. Broomall, Pa.), or other similar equipment.

Both Evaporimeters are based on the vapor pressure gradient estimation method pioneered by Gert E. Nilsson (e.g., Nilsson, G. E., Measurement of water exchange through skin, Med Biol Eng Comput 1977, 15:209-218). There are slight dimensional differences and the sensor technology is greatly improved in the DermaLab® TEWL Probe but the underlying principles of the measurement remain the same. Both probes contain two sensors that measure the temperature and relative humidity at two fixed points along the axis normal to the skin surface. This arrangement is such that the device can electronically derive a value that corresponds to evaporative water loss expressed in $gm/(m^2 \cdot hr)$. The Evaporimeter System extracts value of average evaporative water loss rate collected over a twenty-second interval once steady state conditions had been achieved.

Subjects are treated with test compositions on selected volar forearm test areas as described in the Film Durability on Skin Test. Measurements are taken from each of the volar forearm sites prior to treatment and at various time points (for example, at about 1-hour, about 4-hour, about 6-hour, about 12-hour, about 24-hour, about 30-hour, about 36-hour, about 48-hour, or between 48 hours and one week time point) after application of the composition. Measurements are taken following a minimum of 25 minutes acclimation period in a controlled environment with the relative humidity maintained at less than about 50% and temperature maintained at about 19-22° C. Duplicate water loss readings are taken from each site. TEWL properties ($g/(m^2 \cdot hr)$) are calculated based on the data recorded by the instrument.

Optical Measurement Based on Color L*a*b* Test

This test uses a Minolta CR-400 Chroma meter in accordance with the instructions by the manufacturer, which are generally known in the art. Triplicate measurements of L*(D65), a*(D65), and b*(D65) are then collected at >6 different locations of the test articles.

Barrier Protection Test Based on Viral Penetration

Barrier protection test based on viral penetration is performed to evaluate the barrier performance of protective materials, which are intended to protect against blood borne pathogen hazards. Test articles were conditioned for a minimum of 24 hours at 21±5° C. and 60±10% relative humidity (% RH) and then tested for viral penetraton using a ΦX174 bacteriophage suspension. At the end of the test, the observed side of the test article was rinsed with a sterile medium and assayed for the presence of ΦX174 bacteriophage. The viral penetration method complies with ISO 16604. Triplicate readings are taken from each test article.

In certain embodiments, a film generated with the compositions and methods provided herein has particular evaporative water loss. In certain embodiments, the evaporative water loss can be determined using the assay of the Transepidermal Water Loss (TEWL) Measurement Test provided herein.

5.5.9 Barrier Protection Test Based on Chemical Protection Against Nickel Contact Nickel can be detected at the ppm level with a simple spot test containing 1% dimethylglyoxime and 10% ammonium hydroxide solution, which turns pink upon contact with nickel. A 0.2 M solution of nickel (II) sulfate hexahydrate solution is added to a substrate, and both are covered by the test article. The spot test solution is subsequently applied on the test. A change of color to pink indicates that the nickel has penetrated the test article and come in contact with the color solution, or vice versa. In contrast, absence of color change indicates that the test article is not penetrated and that its barrier function is intact.

In certain embodiments, a film generated with the compositions and methods provided herein provides particular barrier protection against nickel contact. In certain embodiments, the barrier protection against nickel contact can be determined using the assay of the barrier protection test based on chemical protection against nickel contact provided herein.

5.5.10 Barrier Protection Test Based on Protection from Ultraviolet Radiation

The presence of the test article could help reduce the skin absorption of ultraviolet light, particularly when the test article contains SPF active ingredients such as titanium dioxide, zinc oxide, avobenzone, octinoxate, octocrylene, homosalate, or oxybenzone.

To prepare the test article for barrier protection against UV radiation, first the test article was deposited onto a blank Cellophane sheet substrate as described earlier in the application of test composition to the selected substrates. Cellophane sheet size 12.78 cm (L)×8.55 cm (W) is employed to match plateholder of UV-Vis Spectrophotometer. Measure UV absorbance with UV-Vis Spectrophotometer from the wavelength 260 nm to 400 nm with 1 nm scan interval. Report absorption data based on averaged value of at least 4 different spot locations.

In certain embodiments, a film generated with the compositions and methods provided herein provides particular barrier protection against UV radiation. In certain embodiments, the barrier protection against UV radiation can be determined using the assay of the barrier protection test based on protection from ultraviolet radiation provided herein.

6 EXAMPLES

6.1 Example 1: Composition Part 1 (Formula P1-001)

TABLE 1

Active Ingredients of Formula P1-001

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 36.50% |
| A | 6 | DMS-HV31 | Monovinyl monohydride dimethicone | 2.50% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.2 Example 2: Composition Part 1 (Formula P1-002)

TABLE 1

Active Ingredients of Formula P1-002

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 36.50% |
| A | 6 | DMS-HV15 | Monovinyl monohydride dimethicone | 2.50% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.3 Example 3: Composition Part 1 (Formula P1-003)

TABLE 1

Active Ingredients of Formula P1-003

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 36.50% |
| A | 6 | DMS-HV12 | Monovinyl monohydride dimethicone | 2.50% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.4 Example 4: Composition Part 1 (Formula P1-004)

TABLE 1

Active Ingredients of Formula P1-004

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 36.50% |
| A | 6 | DMS-HV22 | Monovinyl monophenyl monohydride dimethicone | 2.50% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.5 Example 5: Composition Part 1 (Formula P1-005)

TABLE 1

Active Ingredients of Formula P1-005

| Phase | No. | Component | Description | Wt % |
|---|---|---|---|---|
| A | 1 | Andisil VS 165,000 | 165,000 cSt Vinyl dimethicone | 45.00% |

TABLE 1-continued

Active Ingredients of Formula P1-005

| Phase | No. | Component | Description | Wt % |
|---|---|---|---|---|
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 36.50% |
| A | 6 | VDH-422 | Vinylmethylsiloxane-dimethylsiloxane copolymer, hydride terminated | 2.50% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.6 Example 6: Composition Part 1 (Formula P1-006)

TABLE 1

Active Ingredients of Formula P1-006

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 34.00% |
| A | 6 | DMS-HV31 | Monovinyl monohydride dimethicone | 5.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.7 Example 7: Composition Part 1 (Formula P1-007)

TABLE 1

Active Ingredients of Formula P1-007

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 34.00% |
| A | 6 | DMS-HV15 | Monovinyl monohydride dimethicone | 5.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.8 Example 8: Composition Part 1 (Formula P1-008)

TABLE 1

Active Ingredients of Formula P1-008

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 34.00% |
| A | 6 | DMS-HV12 | Monovinyl monohydride dimethicone | 5.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.9 Example 9: Composition Part 1 (Formula P1-009)

TABLE 1

Active Ingredients of Formula P1-009

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 34.00% |
| A | 6 | DMS-HV22 | Monovinyl monophenyl monohydride dimethicone | 5.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.10 Example 10: Composition Part 1 (Formula P1-010)

TABLE 1

Active Ingredients of Formula P1-010

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.50% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 34.00% |
| A | 6 | VDH-422 | Vinylmethylsiloxane-dimethylsiloxane copolymer, hydride terminated | 5.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.11 Example 11: Composition Part 1 (Formula P1-011)

TABLE 1

Active Ingredients of Formula P1-011

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 29.00% |
| A | 6 | DMS-HV31 | Monovinyl monohydride dimethicone | 10.00% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.12 Example 12: Composition Part 1 (Formula P1-012)

TABLE 1

Active Ingredients of Formula P1-012

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 29.00% |
| A | 6 | DMS-HV15 | Monovinyl monohydride dimethicone | 10.00% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.13 Example 13: Composition Part 1 (Formula P1-013)

TABLE 1

Active Ingredients of Formula P1-013

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 29.00% |
| A | 6 | DMS-HV12 | Monovinyl monohydride dimethicone | 10.00% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.14 Example 14: Composition Part 1 (Formula P1-014)

TABLE 1

Active Ingredients of Formula P1-014

| Phase | No. | Component | Description | Wt % |
|---|---|---|---|---|
| A | 1 | Andisil VS 165,000 | 165,000 cSt Vinyl dimethicone | 45.00% |

TABLE 1-continued

Active Ingredients of Formula P1-014

| Phase | No. | Component | Description | Wt % |
|---|---|---|---|---|
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 29.00% |
| A | 6 | DMS-HV22 | Monovinyl monophenyl monohydride dimethicone | 10.00% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.15 Example 15: Composition Part 1 (Formula P1-015)

TABLE 1

Active Ingredients of Formula P1-015

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.50% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 29.00% |
| A | 6 | VDH-422 | Vinylmethylsiloxane-dimethylsiloxane copolymer, hydride terminated | 10.00% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.16 Example 16: Composition Part 1 (Formula P1-016)

TABLE 1

Active Ingredients of Formula P1-016

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 38.00% |
| A | 6 | DMS-HV31 | Monovinyl monohydride dimethicone | 1.00% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.17 Example 17: Composition Part 1 (Formula P1-017)

TABLE 1

Active Ingredients of Formula P1-017

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 38.00% |
| A | 6 | DMS-HV15 | Monovinyl monohydride dimethicone | 1.00% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.18 Example 18: Composition Part 1 (Formula P1-018)

TABLE 1

Active Ingredients of Formula P1-018

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 38.00% |
| A | 6 | DMS-HV12 | Monovinyl monohydride dimethicone | 1.00% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.19 Example 19: Composition Part 1 (Formula P1-019)

TABLE 1

Active Ingredients of Formula P1-019

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.5% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 38.00% |
| A | 6 | DMS-HV22 | Monovinyl monophenyl monohydride dimethicone | 1.00% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.20 Example 20: Composition Part 1 (Formula P1-020)

TABLE 1

Active Ingredients of Formula P1-020

| Phase | No. | Component | Description | Wt % |
|---|---|---|---|---|
| A | 1 | Andisil VS 165,000 | 165,000 cSt Vinyl dimethicone | 45.00% |
| A | 2 | Andisil VS 10,000 | 10,000 cSt Vinyl dimethicone | 0.50% |
| A | 3 | Andisil XL-17 | 50 cSt Hydrogen dimethicone | 10.00% |
| A | 4 | Aerosil R812s | Silica silylate (fumed silica) | 5.50% |
| A | 5 | Xiameter PMX-1184 | Dimethicone and Trisiloxane | 38.00% |
| A | 6 | VDH-422 | Vinylmethylsiloxane-dimethylsiloxane copolymer, hydride terminated | 1.00% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.21 Example 21: Composition Part 1 (Formula P1-021)

TABLE 1

Active Ingredients of Formula P1-021

| Phase | No. | Component | Description | Wt % |
|---|---|---|---|---|
| A | 1 | Andisil VS 165,000 | 165,000 cSt Vinyl dimethicone | 45.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV31 | Monovinyl monohydride dimethicone | 3.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.22 Example 22: Composition Part 1 (Formula P1-022)

TABLE 1

Active Ingredients of Formula P1-022

| Phase | No. | Component | Description | Wt % |
|---|---|---|---|---|
| A | 1 | Andisil VS 165,000 | 165,000 cSt Vinyl dimethicone | 45.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV15 | Monovinyl monohydride dimethicone | 3.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.23 Example 23: Composition Part 1 (Formula P1-023)

TABLE 1

Active Ingredients of Formula P1-023

| Phase | No. | Component | Description | Wt % |
|---|---|---|---|---|
| A | 1 | Andisil VS 165,000 | 165,000 cSt Vinyl dimethicone | 45.00% |
| A | 2 | Andisil XL-17 | 50 cSt Hydrogen dimethicone | 10.00% |
| A | 3 | Aerosil R812s | Silica silylate (fumed silica) | 5.50% |

TABLE 1-continued

Active Ingredients of Formula P1-023

| Phase | No. | Component | Description | Wt % |
|---|---|---|---|---|
| A | 4 | Xiameter PMX-1184 | Dimethicone and Trisiloxane | 36.50% |
| A | 5 | DMS-HV12 | Monovinyl monohydride dimethicone | 3.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.24 Example 24: Composition Part 1 (Formula P1-024)

TABLE 1

Active Ingredients of Formula P1-024

| Phase | No. | Component | Description | Wt % |
|---|---|---|---|---|
| A | 1 | Andisil VS 165,000 | 165,000 cSt Vinyl dimethicone | 45.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV22 | Monovinyl monophenyl monohydride dimethicone | 3.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.25 Example 25: Composition Part 1 (Formula P1-025)

TABLE 1

Active Ingredients of Formula P1-025

| Phase | No. | Component | Description | Wt % |
|---|---|---|---|---|
| A | 1 | Andisil VS 165,000 | 165,000 cSt Vinyl dimethicone | 45.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | VDH-422 | Vinylmethylsiloxane-dimethylsiloxane copolymer, hydride terminated | 3.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.26 Example 26: Composition Part 1 (Formula P1-026)

TABLE 1

Active Ingredients of Formula P1-026

| Phase | No. | Component | Description | Wt % |
|---|---|---|---|---|
| A | 1 | Andisil VS 165,000 | 165,000 cSt Vinyl dimethicone | 38.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV31 | Monovinyl monohydride dimethicone | 10.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.27 Example 27: Composition Part 1 (Formula P1-027)

TABLE 1

Active Ingredients of Formula P1-027

| Phase | No. | Component | Description | Wt % |
|---|---|---|---|---|
| A | 1 | Andisil VS 165,000 | 165,000 cSt Vinyl dimethicone | 38.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV15 | Monovinyl monohydride dimethicone | 10.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.28 Example 28: Composition Part 1 (Formula P1-028)

TABLE 1

Active Ingredients of Formula P1-028

| Phase | No. | Component | Description | Wt % |
|---|---|---|---|---|
| A | 1 | Andisil VS 165,000 | 165,000 cSt Vinyl dimethicone | 38.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV12 | Monovinyl monohydride dimethicone | 10.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.29 Example 29: Composition Part 1 (Formula P1-029)

TABLE 1

Active Ingredients of Formula P1-029

| Phase | No. | Component | Description | Wt % |
|---|---|---|---|---|
| A | 1 | Andisil VS 165,000 | 165,000 cSt Vinyl dimethicone | 38.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV22 | Monovinyl monophenyl monohydride dimethicone | 10.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.30 Example 30: Composition Part 1 (Formula P1-030)

TABLE 1

Active Ingredients of Formula P1-030

| Phase | No. | Component | Description | Wt % |
|---|---|---|---|---|
| A | 1 | Andisil VS 165,000 | 165,000 cSt Vinyl dimethicone | 38.00% |
| A | 2 | Andisil XL-17 | 50 cSt Hydrogen dimethicone | 10.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | VDH-422 | Vinylmethylsiloxane-dimethylsiloxane copolymer, hydride terminated | 10.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.31 Example 31: Composition Part 1 (Formula P1-031)

TABLE 1

Active Ingredients of Formula P1-031

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 8.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV31 | Monovinyl monohydride dimethicone | 7.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.32 Example 32: Composition Part 1 (Formula P1-032)

TABLE 1

Active Ingredients of Formula P1-032

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 8.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV15 | Monovinyl monohydride dimethicone | 7.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.33 Example 33: Composition Part 1 (Formula P1-033)

TABLE 1

Active Ingredients of Formula P1-033

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 8.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV12 | Monovinyl monohydride dimethicone | 7.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.34 Example 34: Composition Part 1 (Formula P1-034)

TABLE 1

Active Ingredients of Formula P1-034

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 8.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV22 | Monovinyl monophenyl monohydride dimethicone | 7.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.35 Example 35: Composition Part 1 (Formula P1-035)

TABLE 1

Active Ingredients of Formula P1-035

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 8.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | VDH-422 | Vinylmethylsiloxane-dimethylsiloxane copolymer, hydride terminated | 7.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.36 Example 36: Composition Part 1 (Formula P1-036)

TABLE 1

Active ingredients of Formula P1-036

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 5.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV31 | Monovinyl monohydride dimethicone | 10.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.37 Example 37: Composition Part 1 (Formula P1-037)

TABLE 1

Active Ingredients of Formula P1-037

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 5.00% |

TABLE 1-continued

Active Ingredients of Formula P1-037

| Phase | No. | Component | Description | Wt % |
|---|---|---|---|---|
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV15 | Monovinyl monohydride dimethicone | 10.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.38 Example 38: Composition Part 1 (Formula P1-038)

TABLE 1

Active Ingredients of Formula P1-038

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 5.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV12 | Monovinyl monohydride dimethicone | 10.0% |

Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.39 Example 39: Composition Part 1 (Formula P1-039)

TABLE 1

Active Ingredients of Formula P1-039

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 5.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | DMS-HV22 | Monovinyl monophenyl monohydride dimethicone | 10.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.40 Example 40: Composition Part 1 (Formula P1-040)

TABLE 1

Active Ingredients of Formula P1-040

| Phase | No. | Component | Description | Wt % |
|---|---|---|---|---|
| A | 1 | Andisil VS 165,000 | 165,000 cSt Vinyl dimethicone | 43.00% |
| A | 2 | Andisil XL-17 | 50 cSt Hydrogen dimethicone | 5.00% |
| A | 3 | Aerosil R812s | Silica silylate (fumed silica) | 5.50% |
| A | 4 | Xiameter PMX-1184 | Dimethicone and Trisiloxane | 36.50% |
| A | 5 | VDH-422 | Vinylmethylsiloxane-dimethylsiloxane copolymer, hydride terminated | 10.0% |

Components 1-3 & 6 were added to a container and mixed for 2 minutes at 2000 rpm. Then, Component 4 was added to the mixture and mixed for 12 minutes at 2000 rpm (with manual scraping of the walls of the container at every 2-minute interval to ensure complete dispersion of Component 4). Then, Component 5 was slowly added to the mixture and mixed for 30 minutes at 500 rpm.

6.41 Example 41: Composition Part 2 (Formula P2-001)

TABLE 41

Active Ingredients of Formula P2-001

| Phase | No. | Component | Description | Wt % |
|---|---|---|---|---|
| A | 1 | Johnson Matthey C1142AF | Platinum Divinyldisiloxane, Divinyldisiloxane, Vinyl Dimethicone | 99.00% |
| A | 2 | Andisil 2827-186L | Divinyldisiloxane | 1.00% |

Component 2 was added to Component 1 and mixed for 15 minutes at 250 rpm.

6.42 Example 42: Composition Part 2 (Formula P2-002)

TABLE 42

Active Ingredients of Formula P2-002

| Phase | No. | Component | Description | Wt % |
|---|---|---|---|---|
| A | 1 | Shin-Etsu KF995 | Cyclopentasiloxane | 15.89% |
| A | 2 | Kobo Nylon 10-12 | Nylon 12, Isopropyl Titanium Triisostearate | 4.50% |
| A | 3 | Dow Corning DC9045 Elastomer blend | Dimethicone Crosspolymer, Cyclopentasiloxane | 10.00% |
| A | 4 | Shin-Etsu KSG240 | Dimethicone/PEG-10/15 Crosspolymer, Cyclopentasiloxane | 4.00% |

TABLE 42-continued

Active Ingredients of Formula P2-002

| Phase | No. | Component | Description | Wt % |
|---|---|---|---|---|
| A | 5 | Dow Corning FZ2233 | Bis-Isobutyl PEG/PPG-10/7/Dimethicone Copolymer | 0.10% |
| A | 6 | P2-001 | Platinum Divinyldisiloxane, Divinyldisiloxane, Vinyl Dimethicone | 1.01% |
| B | 7 | DI Water | Water | 29.50% |
| B | 8 | Jeecide CAP-4 | Phenoxyethanol, Caprylyl Glycol | 0.50% |
| B | 9 | Glycerin | Glycerin | 4.00% |
| B | 10 | Propylene Glycol | Propylene Glycol | 20.00% |
| B | 11 | Butylene Glycol | Butylene Glycol | 10.00% |
| B | 12 | Sodium Chloride | Sodium Chloride | 0.50% |

Component 2 was slowly added to Component 1 while mixing at 500 rpm, then stirred for 20 minutes at 500 rpm. Components 3-6 were mixed in a separate container for 5 minutes at 500 rpm. The Components 1-2 mixture was added to the container containing the Components 3-6 mixture, then stirred for 10 minutes at 500 rpm. The resultant Components 1-6 mixture is Phase A. In a separate container, Components 7-12 were mixed for 10 minutes at 400 rpm. The resultant Components 7-12 mixture is Phase B. Phase B was then slowly added to Phase A while mixing at 500 rpm, then stirred for 15 minutes at 500 rpm. The resultant emulsion is then homogenized for 15 minutes at 1150 rpm.

6.43 Example 43: Composition Part 2 (Formula P2-003)

TABLE 43

Active Ingredients of Formula P2-003

| Phase | No. | Component | Description | Wt % |
|---|---|---|---|---|
| A | 1 | Shin-Etsu KF995 | Cyclopentasiloxane | 10.80% |
| A | 2 | Kobo Nylon 10-12 | Nylon 12, Isopropyl Titanium Triisostearate | 3.60% |
| A | 3 | Dow Corning DC9045 | Dimethicone Crosspolymer, Cyclopentasiloxane | 9.45% |
| A | 4 | Shin-Etsu KSG240 | Dimethicone/PEG-10/15 Crosspolymer, Cyclopentasiloxane | 3.60% |
| A | 5 | Dow Corning FZ2233 | Bis-Isobutyl PEG/PPG-10/7/Dimethicone Copolymer | 0.45% |
| A | 6 | Andisil VS250 | Vinyl Dimethicone | 2.70% |
| A | 7 | Momentive Tospearl 3000A | Methylsilsesquioxane | 10.00% |
| A | 8 | P2-001 | Platinum Divinyldisiloxane, Divinyldisiloxane, Vinyl Dimethicone | 0.90% |
| B | 9 | DI Water | Water | 22.05% |
| B | 10 | Jeecide CAP-4 | Phenoxyethanol, Caprylyl Glycol | 0.45% |
| B | 11 | Propylene Glycol | Propylene Glycol | 18.00% |
| B | 12 | Butylene Glycol | Butylene Glycol | 9.00% |
| B | 13 | Baycusan C1008 | Polyurethane 48, Water | 9.00% |

Component 2 was slowly added to Component 1 while mixing at 500 rpm, then stirred for 20 minutes at 500 rpm. Components 3-6 were mixed in a separate container for 5 minutes at 500 rpm. The Components 1-2 mixture was added to the container containing the Components 3-6 mixture, then stirred for 10 minutes at 500 rpm. Component 7 was slowly added to the Components 1-6 mixture while mixing at 500 rpm, then stirred for 5 minutes at 500 rpm. Component 8 was added to the Components 1-7 mixture and stirred for 5 minutes at 500 rpm. The resultant Components 1-8 mixture is Phase A. In a separate container, Components 9-13 were mixed for 10 minutes at 400 rpm. The resultant Components 9-13 mixture is Phase B. Phase B was then slowly added to Phase A while mixing at 500 rpm, then stirred for 15 minutes at 500 rpm. The resultant emulsion was then homogenized for 15 minutes at 1150 rpm.

6.44 Example 44: Composition Part 2 (Formula P2-004)

TABLE 44

Active Ingredients of Formula P2-004

| Phase | No. | Component | Description | Wt % |
|---|---|---|---|---|
| A | 1 | Shin-Etsu KF995 | Cyclopentasiloxane | 11.39% |
| A | 2 | Kobo Nylon 10-12 | Nylon 12, Isopropyl Titanium Triisostearate | 3.80% |
| A | 3 | Dow Corning DC9045 | Dimethicone Crosspolymer, Cyclopentasiloxane | 9.975% |
| A | 4 | Shin-Etsu KSG240 | Dimethicone/PEG-10/15 Crosspolymer, Cyclopentasiloxane | 3.80% |
| A | 5 | Dow Corning FZ2233 | Bis-Isobutyl PEG/PPG-10/7/Dimethicone Copolymer | 0.475% |
| A | 6 | Andisil VS250 | Vinyl Dimethicone | 2.85% |
| A | 7 | Momentive Tospearl 3000A | Methylsilsesquioxane | 5.00% |
| A | 8 | P2-001 | Platinum Divinyldisiloxane, Divinyldisiloxane, Vinyl Dimethicone | 0.96% |
| B | 9 | DI Water | Water | 23.275% |
| B | 10 | Jeecide CAP-4 | Phenoxyethanol, Caprylyl Glycol | 0.475% |
| B | 11 | Propylene Glycol | Propylene Glycol | 19.00% |
| B | 12 | Butylene Glycol | Butylene Glycol | 9.50% |
| B | 13 | Baycusan C1008 | Polyurethane 48, Water | 9.50% |

Formula P2-004 was prepared using the same method as Formula P2-003.

6.45 Example 45: Second Part (Formula P2-005)

TABLE 45

Active Ingredients of Formula P2-005

| Phase | No. | Component | Description | Wt % |
|---|---|---|---|---|
| A | 1 | Dow Corning DC9045 | Dimethicone Crosspolymer, Cyclopentasiloxane | 41.18% |
| A | 2 | Shin-Etsu KSG240 | Dimethicone/PEG-10/15 Crosspolymer, Cyclopentasiloxane | 29.41% |
| A | 3 | Dow Corning FZ2233 | Bis-Isobutyl PEG/PPG-10/7/Dimethicone Copolymer | 5.88% |
| A | 4 | Andisil VS250 | Vinyl Dimethicone | 17.65% |
| A | 5 | P2-001 | Platinum Divinyldisiloxane, Divinyldisiloxane, Vinyl Dimethicone | 5.88% |

Each component was added and mixed altogether for 15 minutes at 250 rpm.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

We claim:

1. A composition for the formation of a film over the skin of a subject, comprising:
   a. a bifunctional organopolysiloxane polymer selected from a group consisting of monovinyl monophenyl monohydride dimethicone, vinylmethylsiloxane-dimethylsiloxane copolymer (hydride terminated), and monovinyl monohydride dimethicone;
   b. a reinforcing constituent suitable for formation of a film on the subject's skin; and
   c. an organopolysiloxane with at least two alkenyl functional groups or at least one alkynyl functional group, either at a terminal of the organopolysiloxane or at a side chain of the organopolysiloxane or both; and
   wherein the bifunctional organopolysiloxane polymer is present in an amount of from about 1% to about 10% by weight of the total weight of the composition.

2. The composition of claim 1, wherein the vinyl group or the hydride group are terminal groups.

3. The composition of claim 1, wherein the bifunctional organopolysiloxane polymer has a degree of polymerization of at least 20 and a dispersity index of less than about 1.2.

4. The composition of claim 3, wherein the degree of polymerization is from about 20 to about 200.

5. The composition of claim 1, wherein the film has no crosslinking.

6. The composition of claim 5, wherein the film is formed via hydrosilylation step-growth polymerization of the bifunctional organopolysiloxane polymer.

7. The composition of claim 5, wherein the bifunctional organopolysiloxane polymer is capable of reacting with a metal catalyst to form the film over the subject's skin.

8. The composition of claim 7, wherein the metal catalyst is a platinum catalyst.

9. The composition of claim 1, wherein the reinforcing constituent is fumed silica.

10. The composition of claim 1, further comprising an agent, wherein the agent is anti-oxidants, vitamins, vitamin D3 analogues, retinoids, minerals, mineral oil, petroleum jelly, fatty acids, plant extracts, polypeptides, antibodies, proteins, sugars, humectants, emollients, or a combination thereof.

11. The composition of claim 1, further comprising an agent, wherein the agent is a cosmetic agent.

12. The composition of claim 11, wherein the cosmetic agent is a moisturizer, a sunscreen, a UV protecting agent, a skin-protectant agent, a skin-soothing agent, a skin-lightening agent, a skin-brightening agent, a skin-softening agent, a skin-smoothening agent, a skin-bleaching agent, a skin-exfoliating agent, a skin-tightening agent, a cosmeceutical agent, a vitamin, an anti-oxidant, a cell-signaling agent, a cell-modulating agent, a cell-interacting agent, a skin tanning agent, an anti-aging agent, an anti-wrinkle agent, a spot reducer, an alpha-hydroxy acid, a beta-hydroxy acid, a ceramide, or a combination thereof.

13. The composition of claim 1, wherein said reinforcing constituent is selected from the group consisting of surface treated mica, zinc oxide, titanium dioxide, aluminum oxide, clay, and silica.

14. A kit for the formation of a film over the skin of a subject, wherein the kit comprises a) a first container comprising the composition of claim 1; and b) a second container comprising metal catalyst.

15. The composition of claim 1, wherein the bifunctional organopolysiloxane polymer is monovinyl monophenyl monohydride dimethicone.

16. The composition of claim 1, wherein the bifunctional organopolysiloxane polymer is vinylmethylsiloxane-dimethylsiloxane copolymer (hydride terminated).

17. The composition of claim 1, wherein the bifunctional organopolysiloxane polymer is monovinyl monohydride dimethicone.

18. The composition of claim 17, wherein the monovinyl monohydride dimethicone has formula

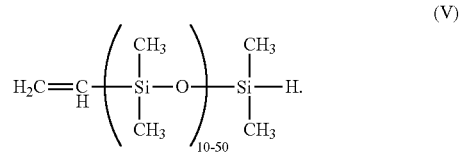

(V)

19. The composition of claim 1, wherein the bifunctional organopolysiloxane polymer is present in an amount of about 1%, about 2.5%, about 3%, about 5%, about 7%, or about 10% by weight of the total weight of the composition.

20. The composition of claim 1, wherein the organopolysiloxane with at least two alkenyl functional groups or at least one alkynyl functional group has formula (I):

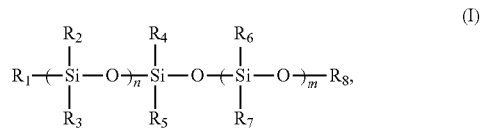

(I)

wherein at least two of $R_1$, $R_4$, $R_5$ and $R_8$ are alkenyl groups or at least one of $R_1$, $R_4$, $R_5$ and $R_8$ is alkynyl group;
the rest of $R_1$, $R_4$, $R_5$ and $R_8$ are $C_{1-20}$ alkyl groups;
$R_2$, $R_3$, $R_6$ and $R_7$ are $C_{1-20}$ alkyl groups; and
the sum of n and m is between 2 and 1,000,000.

* * * * *